US012611419B2

(12) United States Patent
Halbherr et al.

(10) Patent No.: US 12,611,419 B2
(45) Date of Patent: Apr. 28, 2026

(54) LIPOSOMAL COMPOSITION FOR USE IN A METHOD OF TREATING PARKINSON'S DISEASE

(71) Applicant: INNOMEDICA HOLDING AG, Zug (CH)

(72) Inventors: Stéfan Jonathan Halbherr, Wabern (CH); Camille Françoise Peitsch, Bösingen (CH)

(73) Assignee: INNOMEDICA HOLDING AG, Zug (CH)

( * ) Notice: Subject to any disclaimer, the term of this patent is extended or adjusted under 35 U.S.C. 154(b) by 366 days.

(21) Appl. No.: 18/181,163

(22) Filed: Mar. 9, 2023

(65) Prior Publication Data

US 2023/0210875 A1 Jul. 6, 2023

Related U.S. Application Data

(63) Continuation-in-part of application No. 16/956,239, filed as application No. PCT/EP2018/086352 on Dec. 20, 2018, now Pat. No. 11,607,385.

(30) Foreign Application Priority Data

Dec. 21, 2017 (EP) .................................... 17209738
Jan. 18, 2023 (EP) .................................... 23152217

(51) Int. Cl.
*A61K 31/688* (2006.01)
*A61K 31/575* (2006.01)
*A61P 25/28* (2006.01)

(52) U.S. Cl.
CPC .......... *A61K 31/688* (2013.01); *A61K 31/575* (2013.01); *A61P 25/28* (2018.01)

(58) Field of Classification Search
CPC ........................................................ A61P 25/28
See application file for complete search history.

(56) References Cited

U.S. PATENT DOCUMENTS

| | | | | |
|---|---|---|---|---|
| 4,247,547 | A | 1/1981 | Marks | |
| 5,849,326 | A | 12/1998 | Inokuchi et al. | |
| 6,083,920 | A | 7/2000 | Rosenberg | |
| 11,607,385 | B2 * | 3/2023 | Halbherr | A61P 25/28 |
| 2005/0137223 | A1 | 6/2005 | Fan et al. | |
| 2007/0122466 | A1 * | 5/2007 | Chancellor | A61K 9/127 424/450 |

(Continued)

FOREIGN PATENT DOCUMENTS

| | | | |
|---|---|---|---|
| CN | 1128951 | A | 8/1996 |
| CN | 1833633 | A | 9/2006 |

(Continued)

OTHER PUBLICATIONS

J.S. Schneider. "GM1 Ganglioside in the Treatment of Parkinson's Disease." Annals of the New York Academy of Sciences, vol. 845, Jun. 1998, pp. 363-373 and a cover page. (Year: 1998).*

(Continued)

*Primary Examiner* — Isaac Shomer
(74) *Attorney, Agent, or Firm* — Finch & Maloney PLLC

(57) ABSTRACT

A method of treating Parkinson's disease in a subject in need thereof. The method comprises administering a liposomal composition, comprising sphingomyelin in a lipid bilayer and a therapeutically effective amount of GM1, to the subject.

17 Claims, 13 Drawing Sheets

(56) References Cited

U.S. PATENT DOCUMENTS

Figure 1:
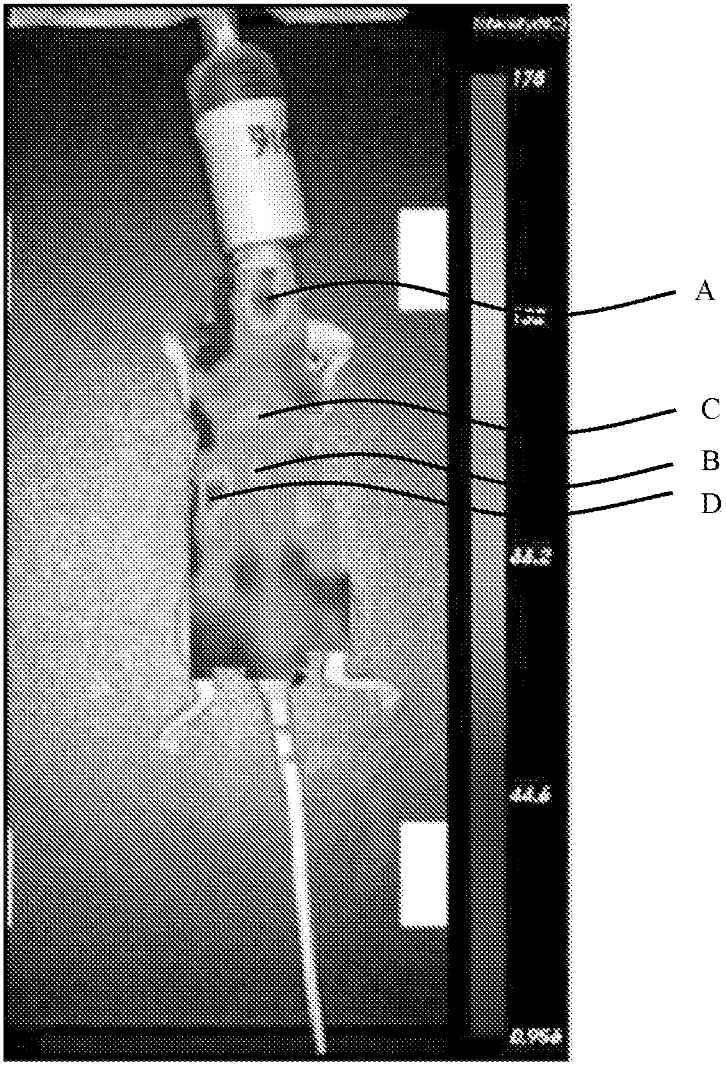

| | | | | |
|---|---|---|---|---|
| 2007/0154539 | A1 | 7/2007 | Fountain | |
| 2011/0250266 | A1* | 10/2011 | Barenholz | A61P 29/00 424/450 |
| 2012/0037564 | A1* | 2/2012 | Tullis | C12N 7/00 210/635 |
| 2012/0220763 | A1* | 8/2012 | Schneider | C12P 19/26 536/53 |
| 2013/0216606 | A1 | 8/2013 | Venkatraman et al. | |
| 2014/0004172 | A1 | 1/2014 | Masserini et al. | |
| 2014/0205543 | A1* | 7/2014 | Penate-Medina | A61K 49/0084 424/9.1 |
| 2015/0267204 | A1* | 9/2015 | Collard | A61P 11/00 435/375 |
| 2021/0077398 | A1* | 3/2021 | Halbherr | A61P 25/28 |
| 2024/0122853 | A1* | 4/2024 | Moon | A61K 31/475 |

FOREIGN PATENT DOCUMENTS

| | | | | |
|---|---|---|---|---|
| EP | 2377872 | A1 | 10/2011 | |
| IT | NA20100046 | A1 | 3/2012 | |
| WO | 1995/025736 | A1 | 9/1995 | |
| WO | 2007/044748 | A2 | 4/2007 | |
| WO | 2008/033253 | A2 | 3/2008 | |
| WO | 2009/150686 | A1 | 12/2009 | |
| WO | 2013/018091 | A1 | 2/2013 | |
| WO | 2014/000857 | A1 | 1/2014 | |
| WO | WO-2019122220 | A1 * | 6/2019 | A61K 31/688 |

OTHER PUBLICATIONS

E Salvati, F Re, S Sesana, I Cambianca, G Sancini, M Masserini, M Gregori. "Liposomes functionalized to overcome the blood-brain barrier and to target amyloid-β peptide: the chemical design affects the permeability across an in vitro model." International Journal of Nanomedicine, vol. 8, pp. 1749-1758. (Year: 2013).*

J.S. Schneider. "GM1 Ganglioside in the Treatment of Parkinson's Disease." Annals of the New York Academy of Sciences, vol. 845, Jun. 1998, pp. 363-373 and a cover page. (Year: 1998).*

E Salvati, F Re, S Sesana, I Cambianca, G Sancini, M Masserini, M Gregori. "Liposomes functionalized to overcome the blood-brain barrier and to target amyloid-β peptide: the chemical design affects the permeability across an in vitro model." International Journal of Nanomedicine, vol. 8, pp. 1749-1758. (Year: 2013).*

Devin T. Wiley, Paul Webster, Aaron Gale, and Mark E. Davis. "Transcytosis and brain uptake of transferrin-containing nanoparticles by tuning avidity to transferrin receptor." Proceedings of the National Academy of Sciences, vol. 110, No. 21, May 21, 2013, pp. 8662-8667 and supplemental pp. 1-11. (Year: 2013).*

J.S. Schneider. "GM1 Ganglioside in the Treatment of Parkinson's Disease." Annals of the New York Academy of Sciences, vol. 845, Jun. 1998, pp. 363-373 and a cover page. (Year: 1998).*

E Salvati, F Re, S Sesana, I Cambianca, G Sancini, M Masserini, M Gregori. "Liposomes functionalized to overcome the blood-brain barrier and to target amyloid-β peptide: the chemical design affects the permeability across an in vitro model." International Journal of Nanomedicine, vol. 8, pp. 1749-1758. (Year: 2013).*

Devin T. Wiley, Paul Webster, Aaron Gale, and Mark E. Davis. "Transcytosis and brain uptake of transferrin-containing nanoparticles by tuning avidity to transferrin receptor." Proceedings of the National Academy of Sciences, vol. 110, No. 21, May 21, 2013, pp. 8662-8667 and supplemental pp. 1-11. (Year: 2013).*

Annie-Louise Robson et al. "Advantages and Limitations of Current Imaging Techniques for Characterizing Liposome Morphology." Frontiers in Pharmacology, vol. 9, Article 80, Feb. 2018, pp. 1-8. (Year: 2018).*

C. Saraiva et al., "Nanoparticle-mediated brain drug delivery: Overcoming blood-brain barrier to treat neurodegenerative diseases", Journal of Controlled Release, 235, May 18, 2016, pp. 34-47, See Spec., p. 2.

R. Meir et al., "Design principles for noninvasive, longitudinal and quantitative cell tracking with nanoparticle-based CT imaging", Nanomedicine: Nanotechnology, Biology and Medicine, vol. 13, Issue 2, Feb. 2017, pp. 421-429, See Spec., p. 2.

C. Sacks et al., "The Failure of Solanezumab—How the FDA Saved Taxpayers Billions", New England Journal of Medicine, 2017; 376, pp. 1706-1708, See Spec., p. 2.

A. Abbot et al., "Leading Alzheimer's theory survives drug failure", News in Focus, vol. 54, Nature, Dec. 1, 2016, pp. 15-16, See Spec., p. 2.

E. Siemers et al., "Phase 3 solanezumab trials: Secondary outcomes in mild Alzheimer's disease patients", Alzheimer's & Dementia, 12 (2016) pp. 110-120, See Spec., p. 3.

J. Schneider et al., "A randomized, controlled, delayed start trial of GM1 ganglioside in treated Parkinson's disease patients", Journal of the Neurological Science, vol. 324, Issues 1-2, Jan. 15, 2013, pp. 140-148, See Spec., p. 4.

D. Lammertse, "Clinical trials in spinal cord injury: lessons learned on the path to translation. The 2011 International Spinal Cord Society Sir Ludwig Guttmann Lecture", Spinal Cord, 51, 2-9, Nov. 20, 2012, See Spec., p. 4.

H. Huang et al., Clinical Neurorestorative Therapeutic Guidelines for Spinal Cord Injury (INAR/CANR version 2019), Journal of Orthopaedic Translation, 20, Nov. 11, 2019, pp. 14-24, See Spec., p. 4.

T. Ariga., "The Pathogenic Role of Ganglioside Metabolism in Alzheimer's Disease-Cholinergic Neuron-Specific Gagliosides and Neurogenesis", Molecular Neurobiology, 54, Jan. 9, 2016, pp. 623-638, See Spec., p. 7.

S. Ong et al., "Evaluation of Extrusion Technique for Nanosizing Liposomes", Pharmaceutics, 8, 36, Dec. 21, 2016, pp. 1-12, See Spec., p. 9 & 14.

M. Aurélio et al., "Traumatic Injuries of the Cervical Spine: Current Epidemiological Panorama", Original Article, Acto Ortop Bras. 2018; 26(2), pp. 123-126, See Spec., p. 11.

Y. Perrie et al., "Manufacturing Methods for Liposome Adjuvants", Methods in Molecular Biology, vol. 1494, Oct. 8, 2016, pp. 127-144, See Spec., p. 14.

R. Ledeen et al., "The multi-tasked life of GM1 ganglioside, a true factotum of nature", CellPress, Special Issue: The Magic of the Sugar Code, Trends in Biochemical Sciences, vol. 40, No. 7, Jul. 2015, pp. 407-418.

N. Haughey, "Sphingolipids in Neurodegeneration", Neuromolecular Medicine, 12(4), Dec. 2010, pp. 301-305.

A. Kharlamov et al., "Semisynthetic Sphingolipids Prevent Protein Kinase C Translocation and Neuronal Damage in the Perifocal Area following a Photochemically Induced Thrombic Brain Cortical Lesion", The Journal of Neuroscience, 13(6), Jun. 1993, pp. 2483-2494.

Z. Jones et al., "Sphigolipids in spinal cord injury", Int. J. Physiol Pathophysiol Pharmacol, 8(2), Aug. 15, 2015, pp. 62-69.

E. Posse de Chaves et al., "Sphingolipids and gangliosides of the nervous system in a membrane function and dysfunction", FEBS Letters, 584, Dec. 17, 2009, pp. 1748-1759.

European Search Report Corresponding to 17209738.8 mailed Jun. 1, 2018.

International Search Report Corresponding to PCT/EP2018/086352 mailed Mar. 14, 2019.

Written Opinion Corresponding to PCT/EP2018/086352 mailed Mar. 14, 2019.

Elisa Salvati et al. "Liposomes functionalized to overcome the blood-brain barrier and to target amyloid-[3 peptide: the chemical design affects the permeability across an in vitro model." International Journal of Nanomedicine, vol. 8, 2013, pp. 1749-1758. (Year: 2013).

Shraddha D. Rege, Thangiah Geetha, Gerald D. Griffin, Tom L.Broderick, and Jeganathan Ramesh Babu. "Neuroprotective effects of resveratrol in Alzheimer disease pathology." Frontiers in Aging Neuroscience, vol. 6 Article 218, Sep. 2014, pp. 1-12. (Year: 2014).

Renzo Mancuso et al. "Resveratrol Improves Motoneuron Function and Extends Survival in SOD1 G93A ALS Mice." Neurotherapeutics, vol. 11, 2014, pp. 419-432. (Year: 2014).

(56) References Cited

OTHER PUBLICATIONS

Debora B Vieira Lionel F Gamarra. "Getting into the brain: liposome-based strategies for effective drug delivery across the blood-brain barrier." International Journal of Nanomedicine, vol. 11, 2016, pp. 5381-5414. (Year: 2016).
Claudia Balducci et al. "Multifunctional Liposomes Reduce Brain B-Amyloid Burden and Ameliorate Memory Impairment in Alzheimer's Disease Mouse Models." The Journal of Neuroscience, Oct. 15, 2014, vol. 34(42), pp. 14022-14031. (Year: 2014).
Laura Bana et al. "Liposomes bi-functionalized with phosphatidic acid and an ApoE-derived peptide affect Af3 aggregation features and cross the blood-brain-barrier: Implications for therapy of Alzheimer disease." Nanomedicine: Nanotechnology, Biology, and Medicine vol. 10 (2014) pp. 1583-1590. (Year: 2014).
Elisa Salvati et al. "Liposomes functionalized to overcome the blood-brain barrier and to target amyloid-8 peptide: the chemical design affects the permeability across an in vitro model." International Journal of Nanomedicine, vol. 8, 2013, pp. 1749-1758. (Year: 2013).
Maika Shilo, Anat Sharon, Koby Baranes, Menachem Motiei, Jean-Paul M Lellouche and Rachela Popovtzer. "The effect of nanoparticle size on the probability to cross the blood-brain barrier: an in-vitro endothelial cell model." Journal of Nanobiotechnology, vol. 13:19, 2015, pp. 1-7. (Year: 2015).
Chandraprakash Dwivedi, Shekhar Verma. "Review on Preparation and Characterization of Liposomes with Application." Journal of Scientific & Innovative Research, vol. 2, Issue 2, Mar.-Apr. 2013, pp. 486-508. (Year: 2013).
James C. Dodge et al. "Giycosphingolipids are modulators of disease pathogenesis in amyotrophic lateral sclerosis." Proceedings of the National Academy of Sciences, vol. 112 No. 26, Jun. 30, 2015, pp. 8100-8105. (Year: 2015).
Andrew D. Wong et al. "The blood-brain barrier: an engineering perspective." Frontiers in Neuroengineering, vol. 6 Article 7, 2013, pp. 1-22. (Year: 2013).
Agrawal Mukta et al., "Recent Advancements in Liposomes Targeting Strategies to Cross Blood-Brain Barrier (BBB) for the Treatment of Alzheimer's Disease", Journal of Controlled Release, Elsevier, Amsterdam, Netherlands, vol. 260, May 24, 2017, pp. 61-77 See European Action.
M. Danaei et al., "Impact of Particle Size and Polydispersity INdex on the Clinical Applications of Lipidic Nanocarrier Systems", Pharmaceutics, vol. 10, No. 2, May 18, 2018, p. 57 See European Search.
Magro Roberta Dal et al., "The Ability of Liposomes, Tailored for Bood-Brain Barrier Targeting, to Reach the Brain is Dramatically Affected by the Disease State",Nanomedicine, vol. 13, No. 6, Jan. 29, 2018, pp. 585-594 See European Action.
European Office Action Corresponding to 18825700.0 mailed Sep. 24, 2021.
H. Blasco et al., "Lipidomics Reveals Cerebrospinal-Fluid Signatures of ALS", Scientific Reports, vol. 7, No. 1, Dec. 15, 2017, https://www.nature.com/articles/s41598-017-17389-9>.
European Search Report Corresponding to 24154120.0 mailed Apr. 30, 2024.
Japanese Office Action Corresponding to JP 2020-554586 mailed Apr. 4, 2023.
Chinese Office Action Corresponding to CN 201880089924.X mailed Nov. 28, 2023.
C. Spuch et al., Liposomes for Targeted Delivery of Active Agetns against Neurodegenerative Diseases (Alzheimer's Disease and Parkinson's Disease), Journal of Drug Delivery, vol. 2011, Article ID 469679, Epub Dec. 13, 2011, 12 pages See Japanese Action.
K. Papadia et al., "How do the physiochemical properties of nanoliposomes affect their interactions with the hCMEC/D3 cellular model of the BBB?", International Journal of Pharmaceutics, vol. 509, Issues 1-2, Epub Jun. 7, 2016, pp. 431-438 See Japanese Action.
Y. Tsou et al., "Drug Delivery to the Brain across the Blood-Brain Barrier Using Nanomaterials", Small, Drug Delivery, vol. 13, Oct. 2017 See Japanese Action.
T. Ishida, "Liposomes", Shikizai Kyokaishi, Jan. 1999, 72 [3], pp. 184-191 See Japanese Action.

* cited by examiner

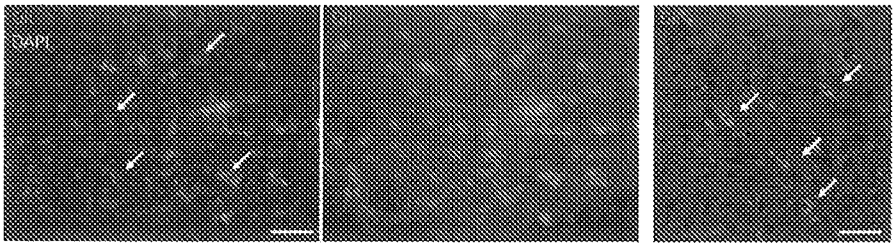
Figure 19a
Figure 19b
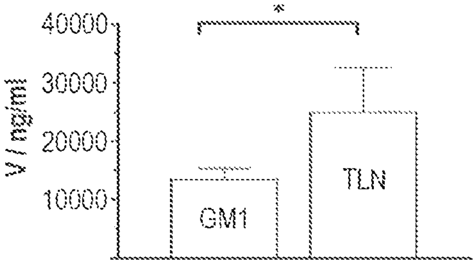
Figure 20

LIPOSOMAL COMPOSITION FOR USE IN A METHOD OF TREATING PARKINSON'S DISEASE

The present invention relates to liposomes, a method of producing liposomes and liposomes for the use as a medicament.

A liposome is a spherical vesicle having at least one lipid bilayer. Liposomes may also be multivesicular liposomes in which one vesicle contains one or more smaller vesicles. The liposome has an aqueous solution core surrounded by a hydrophobic membrane in the form of a lipid bilayer.

The use of liposomes for drug delivery has been proposed for a variety of drugs, particularly those which are administered parenterally. Liposomes have the potential to provide controlled "depot" release of the administered drug over an extended time period, and to reduce side effects of the drug, by limiting the concentration of free drug in the bloodstream. Liposomes can also alter the tissue distribution and uptake of drugs, in a therapeutically favorable way, and can increase the convenience of therapy, by allowing less frequent drug administration. For example, liposomes may transport encapsulated active components directly to the disease site, including tumour cells and sites of inflammation. The active component can be directly released from the liposome at the treatment site. Thus, a lower dosage of the active component is required, and side effects are in consequence limited.

However, depending on the targeted cells, the liposomes need to be modified in order to assure the release of the medicament at the desired treatment site.

The development of drug delivery systems to treat neurodegenerative diseases and spinal cord injuries is particularly challenging, as such systems need to reach the brain and/or the spinal cord. However, due to the restrictive nature of the blood-brain barrier, a special layer of tissue constituting a protective barrier between the central nervous system and the systemic blood circulation, the development of such systems remains rather challenging.

Different efforts have been made in the past to treat neurodegenerative diseases with liposomes. WO 2014/000857 describes the use of liposomes comprising phosphatidic acid and/or cardiolipin as well as apolipoprotein E (ApoE) as the active component in the treatment of Alzheimer's disease. Even though amyloid plaque formation associated with Alzheimer's disease can be reduced at the extra- and intracellular level of the limbic system upon treatment with such liposomes, accumulating evidence from human clinical trials suggests that plaque formation is rather a symptom of disease but not the cause. Multiple phase 3 clinical studies have failed to demonstrate that eliminating plaques slows down disease progression in humans. Recent scientific literature suggests that the particle size of 100 nm described in WO 2014/000857 is too large to efficaciously pass the blood-brain barrier (Saraiva C. et al. 2016 J Controlled Release; Betzer O. et al. 2017 Nanomedicine (London)).

In the example of Alzheimer's disease, further efforts to develop treatment have been undertaken. One recent example is the development of an antibody-based therapy against Alzheimer intending to clear beta-amyloid plaques. However, accumulating evidences from clinical trials suggest that monoclonal antibodies aiming at amyloid-beta clearance do not provide benefits to Alzheimer patients (N Engl J Med. 2017 May 4; 376(18):1706-1708. and Nature. 2016 Nov. 23; 540(7631):15-16. and Alzheimers Dement. 2016 February; 12(2):110-120. Therefore, the need to find alternative approaches for the treatment of Alzheimer's disease persists.

WO 2008/033253 A2 describes the use of liposome complexes for delivering pharmaceutical agents across the blood-brain barrier for the treatment of neurodegenerative diseases. The liposomes are prepared from phospholipids and are associated with a pharmaceutical agent. Further, the liposomes are modified with sialic acid-containing molecules, such as gangliosides, attached to the liposomes. The sialic acid-containing molecule may serve as a linker between the targeting agent, such as antibody based agents or peptides analogues, and the external surface of the liposome or may be attached to the external surface of the liposome to prevent scavenging of the liposome by the body's reticulo-endothelial system. In any case, according to WO 2008/033253, sialic acid-containing molecules are required for ensuring transportation of the targeting agent to the brain.

WO2007/044748 discloses a pharmaceutical composition of liposomes containing sphingomyelin to treat disorders involving neuropathic pain and aberrant muscle contractions associated with bladder hyperactivity disorders. The liposomes are produced by thin film hydration.

WO2009/150686 discloses liposomes which are capable of effectively binding beta amyloid peptide and are useful for the treatment, prevention and diagnosis of Alzheimer's disease. The liposomes are produced by extrusion.

The drawback of such liposomes is a rather laborious and costly industrial scale production. Moreover, the targeting moiety—chemically linked to the liposomal surface—may generate body-foreign molecular structures, which are likely immunogenic and may provoke adverse drug reactions. In contrast, the liposomal membrane of the invention described in this patent application is essentially free of body-foreign molecules, resulting in high biocompatibility.

Another problem lies with the administration of certain active components such as the neuroprotector GM1 ganglioside for the treatment of neurodegenerative diseases. For example, the administration of ganglioside GM1 for indications such as Parkinson's disease has been described to cause difficulties in treatment (J. Neurol. Sci. 2013; 324(1-2): 140-148). Furthermore, the treatment of spinal cord injuries using free GM1 has shown positive outcomes in patients (Spinal Cord (2013) 51, 2-9 and Acta Ortop Bras. 2016 May-June; 24(3):123-6). Due to the pharmacokinetics of GM1, the substance has to be administered subcutaneously or intravenously at high doses. The high dose and route of administration make patients prone to certain types of adverse reactions, such as local pain and swelling at the site of injection, erythema, pruritus and hematoma. It is desirable to avoid such side effects and to avoid the use of high amounts of GM1.

Therefore, there is an unmet medical need for an effective drug delivery systems, which can transport active components to the brain and to the spinal cord for the treatment of neurodegenerative diseases, spinal cord injuries and other neurological disorders. There is in particular a need to provide delivery systems that can overcome the restrictive mechanism imposed by the blood-brain barrier. Ideally, the delivery system can be administered non-parenterally, thus avoiding the risks and inconveniences associated with parenteral administration.

It is thus an object of the present invention to address those needs and to provide liposomes suitable as active components and/or as carrier systems in the treatment of neurodegenerative diseases and spinal cord injuries. It is another object of the present invention to provide a method of producing such liposomes and provide the use of such liposomes as a medicament.

The objects have been solved by liposomes, a method for producing liposomes and liposomes for the use as medicament as outlined below.

The invention relates to liposomes, which comprise sphingomyelin (SM) in the lipid bilayer and are essentially free of gangliosides. In particular, the lipid bilayer of the liposome is essentially free of gangliosides. The liposomes are configured to cross the blood-brain barrier and are suitable for the treatment of neurodegenerative diseases and spinal cord injuries. The different properties of the liposome which render it suitable to configure the blood-brain barrier are described below in more detail.

Sphingomyelin belongs to the group of phospholipids and sphingolipids. It makes up about 10% of the lipids of the brain. Sphingomyelin tends to be in greatest concentrations in the plasma membrane, and especially in the outer leaflet, of cells.

Figure 4:
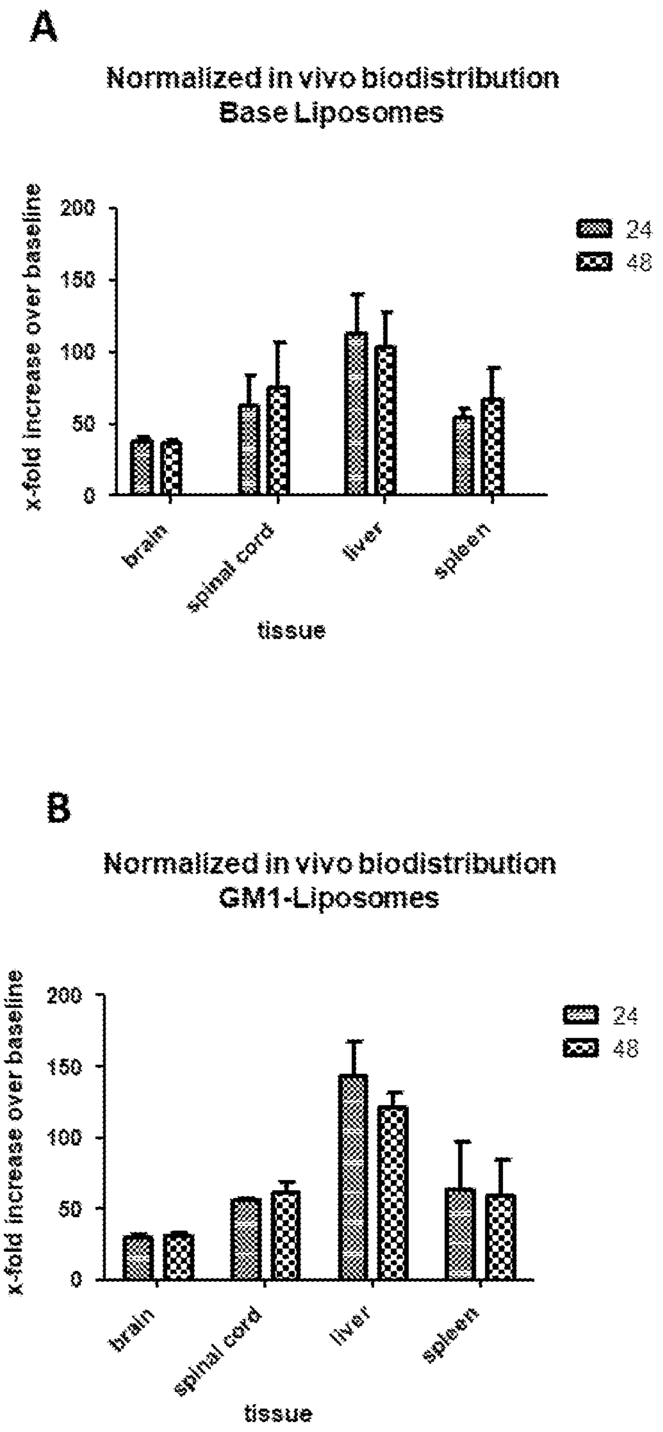

Liposomes comprising sphingomyelin as described in this invention show enhanced stability and enhanced biological properties. These liposomes can act as a medicament. The liposomes may also act as drug carrier system with enhanced pharmacokinetics and therapeutic properties. Surprisingly, it was found that liposomes essentially free of gangliosides are very efficient in crossing the blood-brain barrier and, after administration, can be found in the brain and spinal cord. Moreover, it has been demonstrated that the crossing efficacy is increased compared to liposomes comprising a significant amount of ganglioside (FIG. 4). Thus, an additional modification with ganglioside is not necessary to cross the blood-brain barrier. The liposomes according to the invention are exceptionally suitable as medicament and/or drug carriers for active components directed to the treatment of neurodegenerative diseases and spinal cord injuries.

"Essentially free" in the context of the invention refers to an amount of ganglioside less than 5% mol, preferably even less than 3% mol and most preferably less than 1% mol. It may also be that the liposomes are free of ganglioside.

Sphingomyelin used for the purpose of the present invention can be obtained either by way of synthesis or by way of extraction from natural based components, in particular components of animal origin. Preferably, the sphingomyelin used for the purpose of the present invention is Palmitoyl-D-erythro-sphingosine-1-phosphocholine. Palmitoyl-D-erythro-sphingosine-1-phosphocholine corresponds to the body's own sphingomyelin type phospholipids (d18:1/16:0), resulting in an improved uptake of the liposome into the body, and in particular into the brain and spinal cord. Furthermore, its C16 chain provides a high liposomal stability.

It was further found that the liposomes can be metabolized in clearing organs such as spleen and liver and are thus removed from the body after treatment, avoiding long-term accumulation.

The liposomes may additionally comprise cholesterol (Chol). Preferably, the ratio of sphingomyelin and cholesterol in the liposome may vary between 60-40% mol and 45-55% mol respectively. Liposomes comprising sphingomyelin and cholesterol show an enhanced circulation lifetime. They have improved pharmacokinetics and therapeutic characteristics. They are biocompatible and biodegradable. Sphingomyelin-cholesterol interaction may lead to cholesterol/sphingolipid-enriched nano- and micro-domains (referred to as membrane "rafts") in the plane of plasma and other organelle (e.g. Golgi) membrane. These domains play an important role in regulating synaptic functions and synapse formation, neurotransmitter release and synaptic plasticity (Mol Neurobiol. 2017 January; 54(1):623-638).

The liposomes may essentially be free of surface modifications. By "essentially free" in the context of the modification, it is meant that the modification constitute less than 5% mol of the liposome, preferably even less than 3% mol and most preferably less than 1% mol. The liposome may also be completely free of surface modifications. The surface modification referred to are folic acid, peptides, antibodies, sugars, polyethylene glycol, monoclonal antibodies, fractions of monoclonal antibodies or surface proteins.

Side effects, caused by such modification, can thus be avoided. With this present innovation, a smaller liposomal diameter can be reached allowing a facilitated crossing of the blood-brain barrier. Moreover, the risks of an immune reaction may be lower when the body's own lipids are used. Liposomes without surface modification provide in this case a higher biological compliance avoiding amongst others an enhanced clearance rate. According to the current state of the art, the liposomal surface modification and active targeting is technically very challenging, which may also lead to inefficient biodistributions and lower cost benefit ratio. Further relevant aspects of the present invention may not only be the reduced costs but also the amount of manufacturing steps leading to a facilitated large-scale production.

GM1 is known as neuroprotector. Further, GM1 may interact with a number of proteins that form precipitates in diseases of the central nervous system (CNS) including alpha-synuclein (Parkinson's disease), amyloid-beta (Alzheimer's disease), and huntingtin (Huntington's disease). GM1 and its derivatives are known to penetrate the blood-brain barrier and the neuronal plasma membrane. Administration of LIGA20, a derivative of GM1 has also been demonstrated to reduce Parkinson's symptoms in a rodent model of Parkinson's disease.

Thus, GM1 and derivatives may be inserted in the aqueous compartment of the liposome as an active component in the treatment of neurodegenerative diseases and spinal cord injuries. If incorporated as active component into the aqueous phase of the liposome, GM1 may be present in an amount between 5 and 15% mol, preferably 9 to 11% mol and most preferably 10% mol.

The surface charge of the liposome is an important consideration in the preparation of liposome formulations and a first analytical indication on the insertion of ganglioside GM1. If the ganglioside GM1 is inserted into the liposomal lipid bilayer, the liposome shows a more negative Zeta-potential than the base vesicle lipid bilayer constituted of sphingomyelin and cholesterol. The Zeta-potential can be analysed using a DLS-device and lies in the range of −10 to −60 mV. Liposomes with SM/Chol show a Zeta-potential of −10 mV, SM/Chol/GM1 liposomes show a Zeta-potential of −49 mV. GM1 is negatively charged at pH 5, thus liposomes carrying GM1 become negatively charged.

By measuring the Zeta-potential, it can be determined whether the liposome is essentially free of gangliosides.

Preferably, the liposomes have a mean diameter between 10 and 70 nm, preferably between 10 and 50 nm and most preferably 25 to 35 nm. The mean diameter is determined by cryo transmission electron microscopy (cryoTEM) with a standard deviation of approx. 10 nm.

Liposomes of a mean diameter not exceeding 50 nm are more likely to pass the blood-brain barrier. In addition, they are opsonized less rapidly and at a lower extent than their larger counterparts and are cleared less rapidly by the reticuloendothelial system.

It is preferred that formulations based on such liposomes have a polydispersity index of 0.15, more preferably a polydispersity index from 0.10 to 0.15, and are therefore essentially monodisperse. The polydispersity index is determined by dynamic light scattering (DLS). A polydispersity index 0.15 is superior over the polydispersity indices of liposomal formulations known in the art. Liposomal formulations known in the art, available by extrusion, homogenization, and sonication procedures, typically show polydispersity indices of 0.2 to 0.4 (Gim Ming Ong et al., Evaluation of Extrusion Technique for Nanosizing Liposomes, Pharmaceutics 2016 (8) 36, p. 5). Essentially monodisperse liposomal formulations are beneficial for reproducibility purposes, industrial scale production and compliant with marketing authorization requirements.

The circularity and the lamellarity of the liposomes in a formulation are determined by cryo transmission electron microscopy (cryoTEM). Preferably, the liposomes have a relative circularity of 0.95 and most preferably of 0.98 to 1.00. A circularity of 1.00 represents an absolute circle according to the standard physic rules. Preferably, the liposomes are unilamellar and hold one inner compartment. The liposomes of a liposomal formulation according to the invention are preferably to 90% unilamellar and most preferably 97% to 99% unilamellar.

A homogeneous circularity and unilamellarity of the liposomal dispersion provides a controlled and industrially scalable manufacturing process.

Figure 7:
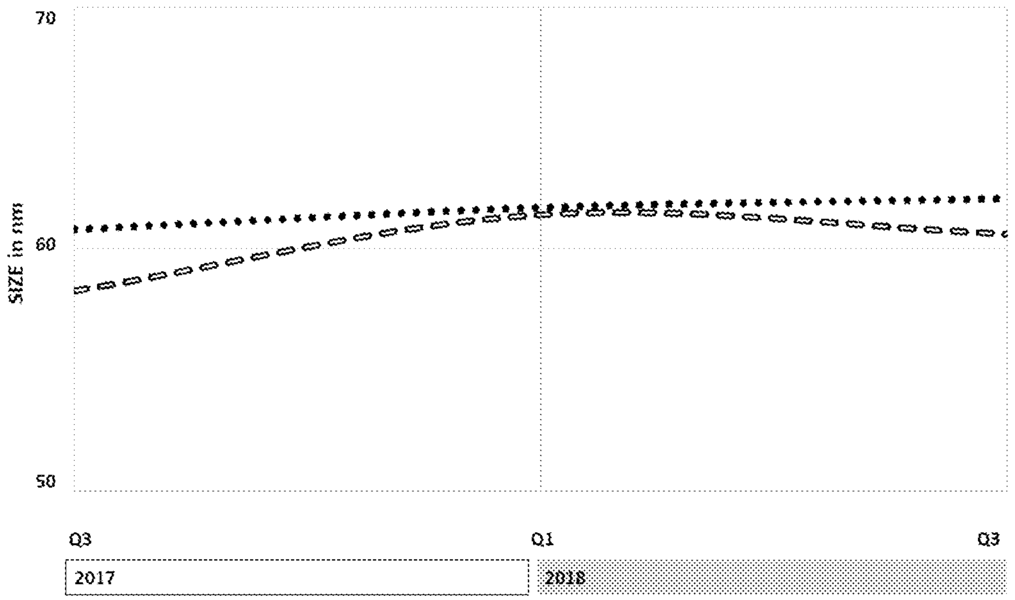

In a preferred embodiment of the invention, the mean diameter of a formulation based on liposomes according to the invention after 6 months, preferably after 12 months, from manufacturing is between 10 and 70 nm, preferably between 10 and 50 nm and most preferably 25 to 35 nm. It is particularly preferred that the mean diameter of the liposomes in a formulation after 6 months, preferably after 12 months from manufacturing is essentially the same as the mean diameter of the liposomes in the formulation immediately after manufacturing (FIG. 7).

Figure 8:
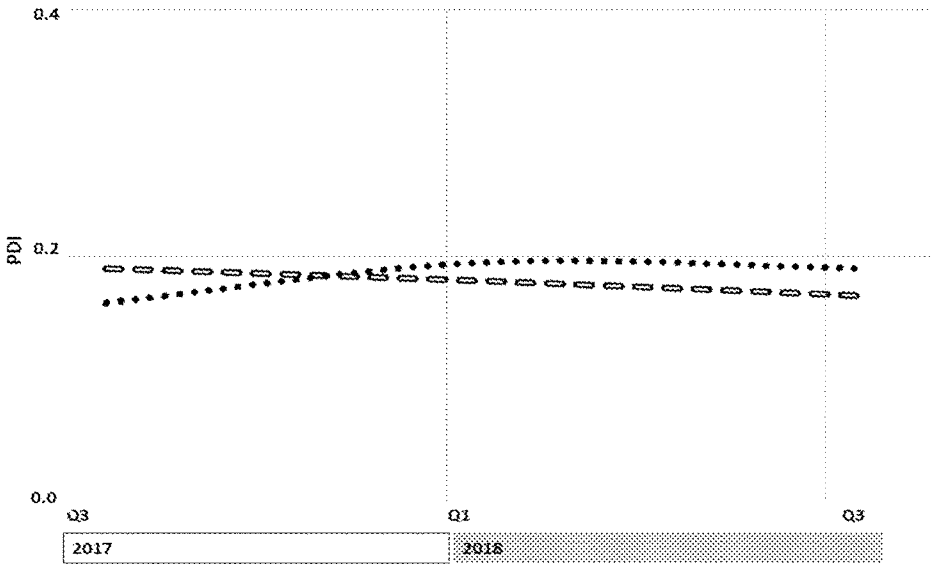

In a preferred embodiment of the invention, the polydispersity index of a formulation based on liposomes according to the invention after 6 months, preferably after 12 months from manufacturing is ≤0.15, preferably 0.1 to 0.15. It is particularly preferred that the polydispersity index of the liposomes after 6 months, preferably after 12 months, from manufacturing is essentially the same as the polydispersity index of the liposomes immediately after manufacturing (FIG. 8).

The liposomes according to the invention are thus particularly stable. The controllability and longevity of the size of liposomes is beneficial for manufacturing, storage, shelf life and patient safety proposes.

The neurodegenerative disease treatable with the liposomes may be chosen from the group: tauopathies, in particular Alzheimer's disease; synucleinopathies, in particular Parkinson's disease; trinucleotide repeat disorder, in particular Chorea Huntington; motor neurone disease, in particular amyotrophic lateral sclerosis; prion diseases, in particular Creutzfeldt-Jakob Disease; diseases of the central nervous system, in particular multiple sclerosis.

Spinal cord injuries as used in the context of the invention refer to all types of spinal cord injuries, complete and incomplete ones.

Spinal cord injuries can be addressed with the liposome of this invention, preferably with the addition of ganglioside, for example GM1, in the inner aqueous compartment of the liposome. GM1, as a neuroprotector, has been shown to restrain the secondary damages (co lateral biochemical damages triggered upon cell death) upon primary damages (mechanical damages). Furthermore, it has been observed to partially restore the sensory part of the concerned area(s) (Acta Ortop Bras. 2016 May-June; 24(3):123-6).

Preferably, at least one active component is comprised and/or encapsulated in the liposomes. It may be also possible to comprise or encapsulate more than one active component. For example, it is possible to comprise or encapsulate active components that show a synergistic effect upon release. At least one active component can also be comprised in the liposomal bilayer and another at least one active component can be encapsulated in the same liposome. It is further possible, that the liposomes are in the form of multivesicular liposome and wherein different active components form part of the same or different smaller vesicles in the multivesicular liposome.

By "comprised in the liposome" it is meant that the active component forms part of the lipid bilayer or is incorporated in the lipid bilayer, respectively. By "encapsulated in the liposome" it is meant, that the active component is enclosed in the inner aqueous compartment of the vesicle.

The term "active component" may include pharmacologically active drugs as well as pro-drugs. Pro-drugs are medications or compounds that, after administration, are metabolized into pharmacologically active drugs.

The active component can be selected from the group consisting of small or large organic or inorganic molecules, nucleic acids, nucleic acids analogues and derivatives, peptides, peptidomimetics, protein, antibodies and antigen binding fragments thereof, monosaccharides, disaccharides, trisaccharides, oligosaccharides, lipids, glycosaminoglycans, an extract made from biological material, and any combination thereof.

The liposome itself can also be an active component, loaded and unloaded.

Those kinds of liposomes offer a broad range of applications. The advantage of liposomes comprising or encapsulating active components can be found in an enhanced therapeutic effect. The liposomes may transfer the active components to the site of action. Since the liposomal membrane is structurally similar to biological membranes, the liposomes may merge with the cellular membranes. Upon merging, the liposomal contents may be emptied into the cell where the active component can act. The use of liposomes as drug carrier system may reduce the side effects associated with the administration of the respective active component and related to high systematic absorption of the active component. The active component can be accumulated at the desired target. The components of the liposome bilayer may be metabolised in the liver and/or spleen.

Preferably, the active component is chosen from the group, consisting of: cholinesterase-inhibitors, in particular donepezil or tacrine; dopamine agonist, in particular bromocriptin or pramipexol; resveratrol; nicotinic derivatives, in particular nicotinamide, nicotinic acid, niacin or NAD+.

Sphingomyelin and/or cholesterol can be chosen as active components too.

In a preferred embodiment of the invention, at least gangliosides, in particular GM1 gangliosides, are encapsulated in the liposome as an active component.

A further aspect of the invention is a method for producing liposomes, preferably liposomes as previously described. The method comprises the steps of:

a) providing lipids and cholesterol in an organic solvent,
b) adding an aqueous liquid,
c) sonication to enable liposome formation,
d) optionally: separating the liposomes, Step c) is carried out such that the liposomes have a mean diameter between 10 and 70 nm, preferably 10 to 50 nm and most preferably 25 to 35 nm, measured by cryo transmission electron microscopy (cryoTEM).

Preferably, the lipids and cholesterol in the organic solvent provided in step a) are not subjected to thin film hydration. By "thin-film hydration" a conventional method for the preparation of liposomes, involving the step of making a thin lipid film in a round-bottom flask by the removal of organic solvent, is meant. Using this method, heterogeneous liposomes are formed upon the addition and agitation of a dispersion medium. Finally, after extrusion through polycarbonate membranes, homogeneous small liposomes are obtained.

In a preferred embodiment of the invention, the liposomes are not subject to a surface modification step, such that the liposomes are essentially free of surface modifications. By "surface modification step" is meant incorporation of folic acid, peptides, antibodies, sugars, polyethylene glycol, monoclonal antibodies, fractions of monoclonal antibodies or surface proteins into the lipid bilayer of the liposome or chemical coupling of such compounds to the liposomal surface.

More preferably, the lipids and cholesterol are not subject to extrusion, i.e. the process does not comprise an extrusion step. By "extrusion" is meant a conventional technique for the preparation of liposomes, where a liposomal formulation is passed through a membrane of defined pore size. Extrusion processes have been discussed in the art as being the method of choice for liposome production (Gim Ming Ong et al., Evaluation of Extrusion Technique for Nanosizing Liposomes, Pharmaceutics 2016 (8) 36; Perrie et al., Manufacturing Methods for Liposome Adjuvants, in; Vaccine Adjuvants: Methods and Protocols, Methods in Molecular Biology, vol. 1494, 2017).

It has been found that liposomes produced by sonication according to this invention are smaller, less polydisperse, more stable and less prone to degradation than liposomes obtainable by conventional techniques.

Preferably, the aqueous solution in step b) is an aqueous buffer solution. Upon adding the aqueous liquid, the solved lipids and cholesterol precipitate. The final ratio of organic solvent in step a) and the aqueous liquid in step b) may be 1:9, meaning that the organic solvent is 10% of the total liquid mixture. Too high solvent concentration in the end product can lead to liposomal instability and/or degradation.

The sonication is preferably performed with an amplitude of at least 60 μm and for at least 1 hour. The sonication can be performed up to 24 hours.

The separation step can be achieved by centrifugation; filtration; field flow fractionation (FFF); dialysis; chromatographic methods, preferably gel-permeations-chromatography.

The liposomes are separated from remaining substances of the liquid mixture, such as organic solvent, salts and/or detergents. Preferably, step d) is performed by buffer exchange. Preferably, steps c) and d) do not require extrusion or any other separation method for the generation of a homogenous liposomal distribution. It is preferred that the liposomes are kept in the original mixture.

The liposome distribution is preferably at least 90% unilamellar and most preferably between 97% and 99% unilamellar. Preferably, the liposomes hold a circularity of 0.95 and most preferably between 0.98 and 1.00. Circularity and the lamellarity have been determined based on images recorded with a cryoTEM JEOL JEM-2100F. In liposomal formulations according to the invention, the ratio of spherical liposomes to broken particles and/or aggregates in weight-% is higher than 9:1, measured by cryotransmission electron microscopy.

The method has the advantage, that small homogeneous liposome can be obtained in one sonication step avoiding thin-film hydration and extrusion and other elaborated and costly steps. Liposomes with a mean diameter of less than 50 nm have a higher tendency to be stable and to cross the blood-brain barrier. In other words, the passing of the blood-brain barrier is facilitated by the small diameter of the liposomes.

At least a part of the lipids used in step a) may be chosen from the group: phospholipids, natural phosphatidylcholine and in particular sphingomyelin; glycolipids, in particular ganglioside; and a combination thereof. It is also possible to use further components such as cholesterol which greatly contribute to the liposomal stability.

These lipids have the advantage of being stable and resistant. Further, they are biocompatible.

Preferably, the organic solvent used in step a) is chosen from the group, consisting of: ethanol, methanol, chloroform and mixtures thereof. Most preferably, organic solvents with high degree of purity are used, e.g. ethanol or methanol absolute >99.99%. Even more preferably, no thin-film hydration is needed.

The used lipids show a good solubility in these organic solvents. By using organic solvents with a high degree of purity contamination of the liposomes with impurities is avoided.

The aqueous liquid used in step b) may be chosen from the group, consisting of: water, aqueous buffer solution, aqueous glycine-solution. Preferably, aqueous buffer solutions with a physiological salt concentration, e.g. PBS (10 mM phosphate, pH 7.2-7.4, 0.9% NaCl) can be used. It is also possible to use the following aqueous buffer solutions: 150 mM ammonium sulphate, 150 nm calcium acetate, 150 mM magnesium acetate, 150 mM manganese acetate, 150 mM iron chloride, or 150 mM copper sulphate.

The aqueous liquid enhances the liposome formation. By using physiological salt concentration, the interior of the liposome resembles the physiological conditions in the body.

Preferably, the organic solvent used in step a) and/or the aqueous liquid used in step b) comprise an active component. The active component is preferably chosen from the groups previously described. The active component is incorporated to the aqueous phase or the solvent, depending on their chemical properties.

It is also possible, that the organic solvent comprises a first active component and the aqueous liquid comprises a second active component. These components may be chosen such that they show a synergistic effect.

A further advantage of having an organic and an aqueous solvent present in the preparation method of the liposomes can be found in a broader access towards active components. Components with a higher solubility in the organic solvent than the aqueous liquid may be equally used and vice versa.

Preferably, the active component should fulfil the following criteria:

- show an amphiphilic solubility in water, meaning having a log D value between −2 and +2,
- comprise at least one weak acid- or base group.

Under certain conditions, it may also be possible to use active components with a log D value >+2. Substances having a log D between −2 and +2 can be encapsulated by remote loading. Molecules with a log D beyond this range may be loaded by membrane encapsulation.

The use of an additionally active component enhances the therapeutic effect. Due to their similarity with cell membranes, the liposomes may merge with the cell membrane and may specifically act as an active component at the target site. The liposomes may also release the encapsulated or comprised active components into the cell after merging of the liposome with the cell membrane.

The liposomes as previously described may be used as a medicament, in particular for use in the treatment of neurodegenerative diseases and spinal cord injuries.

The neurodegenerative disease may be chosen from the group as previously described. The spinal cord injuries refer to all types of spinal cord injuries.

Preferably, the liposomes as previously described, in the treatment of neurodegenerative diseases and spinal cord injuries as previously described, are administered orally or intravenously.

If administered orally, the liposome composition can be in form of a solid or a drinkable solution. It may be in the form of dragees, tablets, granulate, capsules, powder, an emulsion, suspension or syrup. The liposomes as previously described have the advantage of having a stability resisting the conditions associated with passing the gastrointestinal passage. By oral administration, side effects associated with a subcutaneously or intravenously delivery can be avoided.

Further, if administered orally, the liposomal composition can include further ingredients. The addition of flavours would provide a more pleasant taste, enteric coatings e.g. on the tablets would provide an additional protection against the acid. Basic ingredients such as hydrogen carbonate may provide a stomach-friendly administration. Also vitamins or minerals could be included.

The oral administration has the advantage of being easier applicable than intravenously. A patient would be able to take the medicament in accordance with the prescription and without the need of trained personal.

An intravenous administration can be of advantage if uptake of the liposomes through the gastrointestinal track is less favoured, for example due to the patient's health condition.

For intravenous injection, the liposomes may be present in solved or suspended form. The amount of liquid may be in the range of 0.1-20 ml and is dose dependent. The injectable solution can comprise further ingredients, such as stabilising agents. It can also comprise physiological compatible ingredients such as salt, in particular sodium chloride or alcohol, preferably ethanol.

A further aspect of the invention is liposomes as previously described obtainable by a method as previously described.

Parkinson's disease (PD) is a brain disorder that causes unintended or uncontrollable movements, such as shaking, stiffness, and difficulty with balance and coordination. Symptoms usually begin gradually and worsen over time. As the disease progresses, people may have difficulty walking and talking. They may also have mental and behavioural changes, sleep problems, depression, memory difficulties, and fatigue.

The most prominent signs and symptoms of PD occur when neurons in the basal ganglia, an area of the brain that controls movement, become impaired and/or die. Normally, these neurons produce an important brain chemical known as dopamine. When the neurons die or become impaired, they produce less dopamine, which causes the movement problems associated with the disease.

Although there is no cure for PD, medicines, surgical treatment, and other therapies can often relieve some symptoms. Medicines can help treat the symptoms of Parkinson's by increasing the level of dopamine in the brain, by having an effect on other brain chemicals, such as neurotransmitters, which transfer information between brain cells, or by helping control non-movement symptoms.

The main therapy for Parkinson's is levodopa (or L-DOPA). Nerve cells use levodopa to make dopamine to replenish the brain's dwindling supply. Usually, people take levodopa along with another medication called carbidopa. Carbidopa prevents or reduces some of the side effects of levodopa therapy—such as nausea, vomiting, low blood pressure, and restlessness—and reduces the amount of levodopa needed to improve symptoms.

Other medicines to treat Parkinson's symptoms include dopamine agonists to stimulate the production of dopamine in the brain, enzyme inhibitors (e.g., MAO-B inhibitors, COMT inhibitors) to increase the amount of dopamine by slowing down the enzymes that break down dopamine in the brain, amantadine to help reduce involuntary movements and anticholinergic drugs to reduce tremors and muscle rigidity.

Certain types of glycolipids have been identified to play a key role in the development and treatment of PD. Glycolipids are lipids with a carbohydrate attached by a glycosidic bond. Their role in living cells is to maintain the stability of the cell membrane and to facilitate cellular recognition. Glycosphingolipids are a subtype of glycolipids containing the amino alcohol sphingosine. They occur in the nervous system and elsewhere in the body and they are involved in metabolic and pathological changes that accompany PD.

Ganglioside GM1 (monosialotetrahexosylganglioside, CAS: 37758-47-7) is a glycosphingolipid consisting of a branched pentasaccharide made up from one sialyl residue, two galactose residues, one N-acetylgalactosamine residue and a glucose residue at the reducing end attached to N-stearoylsphingosine via a beta-linkage. GM1 has important physiological properties and impacts neuronal plasticity and repair mechanisms, and the release of neurotrophins in the brain (VASQUES, J. F. et al. Gangliosides in nervous system development, regeneration, and pathologies. Neural Regen. Res. 2023, Vol. 18, No. 1, pages 81 to 86). It is an amphiphilic, endogenous molecule found abundantly on the outer leaflets of membranes of all mammalian cells and is particularly enriched on the neuronal plasma membrane (it constitutes 5%±10% of the total lipid mass).

GM1 interacts with the neighboring proteins to modulate intracellular signaling, mainly of biochemical pathways of neuronal differentiation, homeostasis, protection, and restoration. It has been reported to have neurotrophic properties and influences a variety of cellular activities at the level of the plasma membrane as well as intracellularly. In the central nervous system (CNS), GM1 exhibits many ganglioside functions during development, function and repair. It may also counteract neuroinflammation.

Higher gangliosides like GM1 appear only during late stages of organogenesis and foetal growth, hinting towards their integral function to guide formation of a fully functional and young CNS. The possibility of reintroducing this "young CNS"-state—at least in part—from a lipid-based perspective could have therapeutic applications (XU, Y.-H. et al. Multi-system disorders of glycosphingolipid and ganglioside metabolism. J. Lipid Res. 2010, Vol. 51, No. 7, pages 1643 to 1675).

GM1 belongs to the a-series gangliosides and its biosynthesis occurs in the Golgi apparatus. Along with the more complex gangliosides, GM1 is enriched in the pre- and postsynaptic membranes of the synaptic terminals. In addition to regulating nuclear Ca2+-homeostasis (via high-affinity binding of the ganglioside to the sodium/calcium exchanger at the nuclear envelope) and other cellular functions, GM1 modulates neurotrophic activity by associating with receptors TrkA, TrkB, and GDNF (NEWBURN, E. N. et al. GM1 ganglioside enhances Ret signaling in striatum. J. Neurochem. 2014, Vol. 130, No. 4, pages 541 to 554).

The role of GM1 in both the generation and potential treatment of PD has been of particular interest (CHOWDHURY, S. et al. The Key Role of GM1 Ganglioside in Parkinson's Disease. Biomolecules 2022, Vol. 12, No. 173, pages 1 to 9). GM1 deficiency prevents the normal functioning of cells dependent on an adequate level of this ganglioside, resulting in their gradual degeneration and eventual death. Studies in humans suggest GM1 deficiency could be a contributing factor to the development of idiopathic PD. Reductions in GM1 have been reported in the PD post-mortem brain (WU, G. det al. Deficiency of ganglioside GM1 correlates with Parkinson's disease in mice and humans. J. Neurosci. Res. 2012, Vol. 90, No. 10, pages 1997 to 2008). It was further reported that GM1 levels decrease over time in the healthy human brain. In the brain of a PD patient, however, this decrease is particularly pronounced (HUEBECKER, M. et al. Reduced sphingolipid hydrolase activities, substrate accumulation and ganglioside decline in Parkinson's disease. Mol. Neurodegener. 2019, Vol. 14, No. 1, pages 1 to 21).

A decrease in GM1 levels has also been observed in ante-mortem cerebrospinal fluid (CSF) of PD patients (compared to age-matched controls), although it was not significant (17.4% reduction). Similar analysis in blood serum did find a significant reduction in samples from PD patients (LEDEEN, R. et al. Systemic deficiency of GM1 ganglioside in Parkinson's disease tissues and its relation to the disease etiology. Glycoconj. J. 2022, Vol. 39, No. 1, pages 75 to 82).

Transgenic mice wholly or partially deficient in the GM1 family of gangliosides due to disruption of the B4galnt1 gene (GM2 synthase-B4galnt1) have been reported to develop PD features based on behavioural and neuropathological criteria. These include movement deficits (as early as five weeks of age) and histopathological details such as depletion of striatal dopamine, loss of dopamine neurons of the substantia nigra pars compacta, and accumulation of alpha synuclein. Notably, the administration of GM1 ameliorated these pathological CNS manifestations (WU, G. et al. Mice deficient in GM1 manifest both motor and non-motor symptoms of Parkinson's disease; successful treatment with synthetic GM1 ganglioside. Exp. Neurol. 2020, Vol. 329, 113284).

There have been a number of clinical investigations exploring the therapeutic potential of GM1 in PD cohorts. The first was a small pilot study. This was an open-label study in which 10 PD patients received 1000 mg of GM1 by intravenous infusion after their last of three baseline functional assessments, and then self-administered GM1 at a dose of 200 mg/day, by subcutaneous injection, for 18 weeks. Under these conditions, GM1 ganglioside proved to be safe and well tolerated. There were no serious adverse events and none of the patients developed elevated anti-GM1 antibody titres (SCHNEIDER, J. S. et al. GM1 ganglioside treatment of Parkinson's disease: an open pilot study of safety and efficacy. Neurology 1995, Vol. 45, No. 6, pages 1149 to 1154).

That study was followed up by a larger randomized placebo-controlled study involving 45 individuals with mild to moderate PD (using the same GM1 treatment regime as above). In this study, significant differences between groups in the Unified PD Rating Scale (UPDRS) motor scores ($p=0.0001$) and activities of daily living portion (off-period assessment; $p=0.04$) were reported at 16 weeks (SCHNEIDER, J. S. et al. Parkinson's disease: improved function with GM1 ganglioside treatment in a randomized placebo-controlled study. Neurology 1998, Vol. 50, No. 6, pages 1630 to 1636). In a follow-up open-extension study, at the end of 5 years of GM1 use, the investigators concluded that "long-term GM1 use by PD patients is safe and may provide some clinical benefit". Participants generally had lower UPDRS motor scores (assessed during a practically defined "off" period) (SCHNEIDER, J. S. et al. GM1 ganglioside in Parkinson's disease: Results of a five-year open study. J. Neurol. Sci. 2010, Vol. 292, No. 1, pages 45 to 51).

These findings supported the initiation of a larger, delayed start study. Of the 157 individuals screened, 77 were randomized to either early-start or delayed-start of GM1 treatment. The GM1 treatment regime was the same as the previous studies. A separate comparison group of 17 individuals were used as a standard care treatment comparator. At week 24, the early-start group had significant improvement in UPDRS motor scores vs. a significant worsening of scores in the delayed-start group. The early-start group also showed a sustained benefit vs. the delayed-start group at week 72 and at week 120. Both groups exhibited significant symptom worsening during the washout period after 2 years of GM1 treatment. The study demonstrated that long-term administration of GM1 was safe and well tolerated and it reported no increase in anti-GM1 antibody titres in the participants (SCHNEIDER, J. S. et al. A Randomized, Controlled, Delayed Start Trial of GM1 Ganglioside in Treated Parkinson's Disease Patients. J. Neurol. Sci. 2013, Vol. 324, No. 1, pages 140 to 148). 15 participants from the early-start group and 14 participants from the delayed-start group volunteered to be part of a PET (11)C-methylphenidate imaging study (along with the 11 members of the comparator group). The three groups were scanned at baseline, week 24, and 1-2 years later. The results indicated significant slowing of binding loss in several striatal regions of the GM1-treated groups. In some cases, an increased binding was detected after GM1 use (SCHNEIDER, J. S. et al. GM1 ganglioside in Parkinson's disease: Pilot study of effects on dopamine transporter binding. J. Neurol. Sci. 2015, Vol. 356, No. 1, pages 118 to 123).

One of the problems with translating the therapeutic potential of GM1 from preclinical models to the clinic is the ability of this molecule to adequately reach the CNS when administered peripherally. CNS penetrance is severely limited by GM1's amphiphilicity, which hampers the passage across the blood-brain barrier. Thus, novel methods of delivery of GM1 to the CNS are required for translation to the clinic.

Furthermore, despite the promising signs of the studies on GM1, certain side effects (adverse events) stand in the way of GM1's marketability, which need to be overcome. For example, pain, irritation of the skin site and severe haematoma at the injection site occur during treatment with GM1, as the most common mode of administration of GM1 is subcutaneous.

For better bioavailability of GM1 in the CNS, the use of liposomes as vesicles for drug delivery for treating PD has been proposed (WO 2019122220 A1 (INNOMEDICA HOLDING AG) 27.06.2019, pages 7 to 8). However, therapeutically effective formulations and dosing regimens do not yet exist in the state of the art.

It is thus an object of the present invention to address those needs and to provide an improved treatment of PD. In particular, it is an object to reduce the adverse events profile frequently encountered with the frequent subcutaneous administration.

The problems have been solved by using a liposomal GM1 formulation as a medicament, having the features according to the independent claim.

The invention relates to a liposomal composition for use in a method of treating PD, said liposomal composition comprising sphingomyelin in a lipid bilayer and a therapeutically effective amount of monosialotetrahexosylganglioside (GM1), wherein a therapeutically effective dose of said liposomal composition is administered at most every 4 days in a primary mode of administration with at least 3 days between each administration; preferably at most every 6 days in a primary mode of administration with at least 5 days between each administration; most preferably at most every 7 days in a primary mode of administration with at least 6 days between each administration.

A liposomal composition is a composition containing liposomes in addition to other components, wherein one or more of said other components are encapsulated in the liposomes. A liposome is a spherical vesicle having at least one lipid bilayer. Liposomes may also be multivesicular liposomes in which one vesicle contains one or more smaller vesicles. The liposome has an aqueous solution core surrounded by a hydrophobic membrane in the form of a lipid bilayer. Liposomes have the potential to provide controlled release of an encapsulated active pharmaceutical ingredient (API) over an extended period, and to reduce the side effects of the encapsulated ingredients, by limiting the concentration of free ingredients in the blood stream and tissue. Liposomes can also alter the tissue distribution and uptake of APIs, in a therapeutically favorable way, and can increase the convenience of therapy, by allowing less frequent drug administration. For example, liposomes may transport encapsulated APIs directly to the disease site. The active component can be directly released from the liposome at the treatment site. Thus, a lower dosage of the active component is required, and side effects are in consequence limited.

In the case of PD, liposomes comprising an appropriate lipid membrane composition enhance penetration of the blood-brain barrier. The blood-brain barrier comprises the blood vessels that vascularize the CNS and that tightly regulate the movement of ions, molecules, and cells between the blood and the CNS. This leads to increased deposition of APIs that are encapsulated in liposomes in the CNS.

The preparation of the liposomal composition containing GM1 was described in the prior art (WO 2019122220 A1 (INNOMEDICA HOLDING AG) 27.06.2019). In particular, the circularity of the liposomes used for the liposomal composition of the present invention is greater than or equal to 0.95, in particular 0.98-1.00. The circularity of the liposomes in a formulation are determined by cryogenic transmission electron microscopy (CryoTEM).

The lipids from the lipid membrane composition used to form the liposomes of the present invention are all omnipresent in healthy brain tissue. The liposomes of the present invention comprise the lipid sphingomyelin, which belongs to the groups of phospholipids and sphingolipids. It makes up about 10% of the lipids of the brain. Sphingomyelin tends to be in greatest concentrations in the plasma membrane, and especially in the outer leaflet, of biological cells.

As it is understood in the art, a lipid bilayer in a liposome is a thin polar membrane made of two layers of lipid molecules, wherein, in aqueous media, the polar, hydrophilic ends of the lipid molecules are on the top and bottom surface of the membrane and the nonpolar, hydrophobic ends of the lipid molecules are inside the membrane. This membrane forms the shell of a sphere with an aqueous core. An encapsulated compound in a liposome may either be located in the aqueous core of the liposome or it may be located in or at the surface of the membrane.

The API of the present invention, GM1, is partially located in the membrane and partially in the aqueous core of the liposome. As described earlier, it is known in the art that ganglioside GM1 plays a big role in both the generation and potential treatment of PD. The chemical name of GM1 according to the International Union of Pure and Applied Chemistry (IUPAC) is (2S,4S,5R,6R)-5-acetamido-2-[(2S,3R,4R,5S,6R)-5-[(2S,3R,4R,5R,6R)-3-acetamido-5-hydroxy-6-(hydroxymethyl) [(2R,3R,4S,5R,6R)-3,4,5-trihydroxy-6-(hydroxymethyl)oxan yl]oxyoxan-2-yl]oxy-2-[(2R,3S,4R,5R,6R)-4,5-dihydroxy [(E,2R,3S)-3-hydroxy-2-(icosanoylamino)icos-4-enoxy]-2-(hydroxymethyl)oxan-3-yl]oxy-3-hydroxy-6-(hydroxymethyl)oxan yl]oxy-4-hydroxy-6-[(1R,2R)-1,2,3-trihydroxypropyl]oxane carboxylic acid. GM1 has the following structural formula:

Formula 1

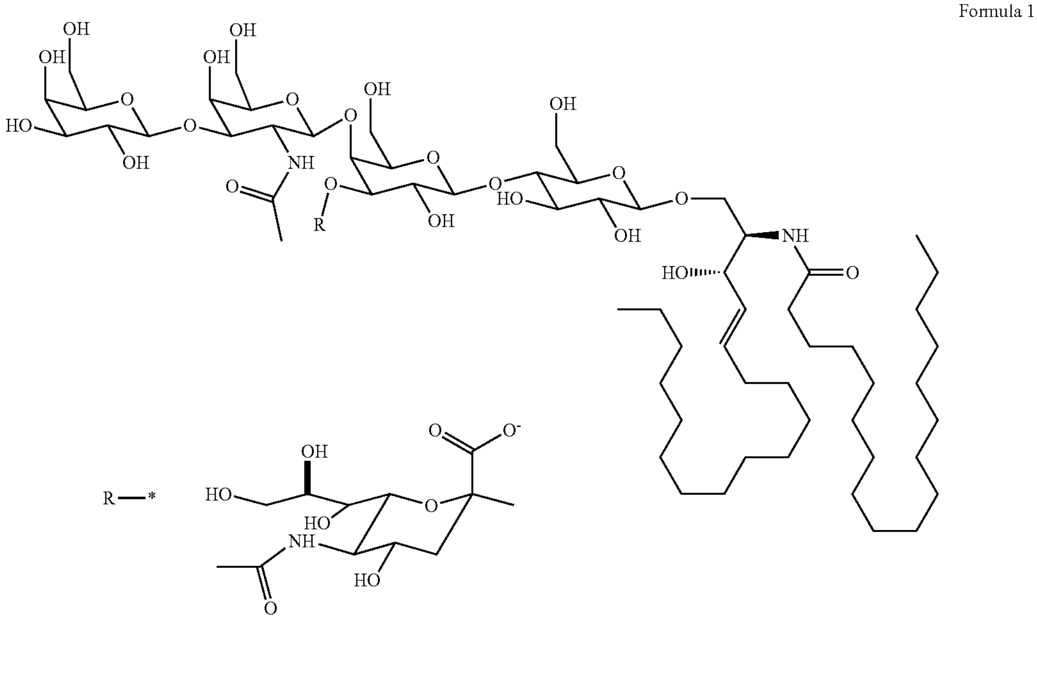

A therapeutically effective amount of monosialotetrahexosylganglioside (GM1) refers to that amount of GM1 which results in at least one of prevention or delay of onset of symptoms of PD in a subject; amelioration of symptoms of PD in a subject; prevention or delay of onset of signs of PD in a subject; amelioration of signs of PD in a subject; or a combination thereof. As it is understood in the art, a symptom is something felt or experienced, such as pain or dizziness. As it is understood in the art, a sign is an objective observable indication of a disease, injury, or abnormal physiological state that may be detected during a physical examination, examining the patient history, or diagnostic procedure. Signs and symptoms are not mutually exclusive.

These symptoms and signs comprise unintended or uncontrollable movements, such as shaking, stiffness, and difficulty with balance and coordination and difficulty with walking and talking. Symptoms are usually assessed using the Movement Disorder Society Unified PD Rating Scale (MDS-UPDRS).

Therapeutic efficacy of PD is usually measured using the MDS-UPDRS system. The system comprises four parts: non-motor aspects of experiences of daily living are assessed in part I in a questionnaire; motor aspects of experiences of daily living are assessed in part II in a questionnaire; a motor examination is performed in part III in a clinical examination (not in a questionnaire); and motor complications from treatment are assessed in part IV in a questionnaire. The higher the MDS-UPDRS value, the more pronounced the disease.

In the context of the present invention, a dose is a measured quantity of a therapeutic agent to be taken at one time, wherein the measured quantity may be administered over a period of time.

In the context of the present invention, a therapeutically effective dose of said liposomal composition is a dose of the liposomal composition that contains an amount of GM1 which results in at least one of prevention or delay of onset of symptoms; or amelioration of symptoms of PD in a subject.

Parkinson's disease (PD) is a brain disorder that causes unintended or uncontrollable movements, such as shaking, stiffness, and difficulty with balance and coordination. Symptoms usually begin gradually and worsen over time. As the disease progresses, people may have difficulty walking and talking. They may also have mental and behavioural changes, sleep problems, depression, memory difficulties, and fatigue.

According to the invention, a dose of the liposomal composition comprising GM1 is administered at most every 4 days in a primary mode of administration with at least 3 days between each administration; preferably at most every 6 days in a primary mode of administration with at least 5 days between each administration; most preferably at most every 7 days in a primary mode of administration with at least 6 days between each administration. "At most every 7 days with at last 6 days between each administration", for example, means that if a dose is administered on a Monday, for example, the next dose of the primary mode of administration will be administered on the following Monday at the earliest.

The primary mode of administration may be any mode of administration that the person skilled in the art deems appropriate to administer the dose over a reasonable period of time.

It has been found that the liposomal composition as GM1 carrier system comprising sphingomyelin as described in this invention lead to enhanced pharmacokinetics and therapeutic properties of the encapsulated GM1.

Without wishing to be bound by theory, the liposomal composition according to the invention increases delivery of GM1 to the CNS, as the penetrability of the blood-brain barrier by the liposomal composition is higher than the penetrability by the non-liposomal GM1. Additionally, intracellular delivery of GM1 is improved as well by encapsulating it in the liposomal composition. Non-liposomal GM1 remains to a larger degree extracellular, as it has a lower penetrability of the cell membrane. The biodistribution of GM1 is thus altered in a favourable manner with the liposomal composition to increase the drug deposition in the CNS.

Furthermore and without wishing to be bound by theory, it was found that the circulation of liposomal GM1 is prolonged compared to non-liposomal GM1, as liposomal GM1 gets metabolized and excreted at a lower rate.

As a consequence of the higher penetrability of both the blood-brain barrier and the cell membrane as well as the prolonged circulation, a smaller amount of GM1 is required to obtain the desired pharmacological effect when employing the liposomal composition compared to non-liposomal GM1. This in turn means that GM1 needs to be administered less frequently.

As it has been discussed earlier, when GM1 is administered by injection, in particular by subcutaneous injection but also by other types of injection, strong pain, severe hematomas and irritation of the skin at the injection site are observed. It was found that smaller amounts of GM1 per dose and/or a lower administration frequency made possible by the liposomal composition result in a reduction of the adverse events profile in PD patients. Less severe or even the absence of pain, hematomas and skin irritation are the result.

Surprisingly, it was found that the serum half-life of the liposomal composition of the invention in venous blood plasma is longer than normally observed for non-PEGylated (PEG: polyethylene glycol) liposomal compositions comprising sphingomyelin. Non-PEGylated liposomal compositions comprising sphingomyelin for use in medical applications reported in literature have a serum half-life of up to 10 h (KRISHNA, R. et al. Liposomal and Nonliposomal Drug Pharmacokinetics after Administration of Liposome-Encapsulated Vincristine and Their Contribution to Drug Tissue Distribution Properties. JPET. 2001, Vol. 298, pages 1206 to 1212; SENIOR, J. et al. Is half-life of circulating liposomes determined by changes in their permeability? FEBS Lett. 1982, Vol. 145, No. 1, pages 109 to 114). According to the literature, one way to prolong the half-life of liposomes in blood plasma is to PEGylate the liposomes (PARK, H. et al. Evolution of drug delivery systems: From 1950 to 2020 and beyond. JCR 2022, Vol. 342, pages 53 to 65). However, the liposomal composition of the invention does not require PEGylation of the liposome and a half-life of up to 30 h is still observed. This shows that with the liposomal composition of the invention, half-lives for non-PEGylated liposomal compositions comprising sphingomyelin are achieved that the skilled person would not expect. This allows longer intervals between administrations without significant loss of therapeutic effect in the time between doses.

In particular, it was found that for the majority of PD patients treated, the liposomal GM1 composition needs to be administered at most every 7 days to achieve a desired therapeutic effect throughout the inter-dose period. Initial findings show that, in certain cases, more frequent administration (e.g. every 4 or every 6 days) is beneficial to maintain a therapeutic effect between doses. This is, however, still an improvement compared to state-of-the-art dosing regimens of twice daily for instance.

The advantages, improved efficacies and reductions in adverse events will be shown in the examples section hereinafter.

In a preferred embodiment, the composition is administered intravenously in the primary mode of administration. It was found that the adverse events can be mitigated not only by the smaller amount of GM1 required and the lower frequency of administration as described above, but also when the common subcutaneous injection is replaced with an intravenous injection. This results in even less pain, hematomas and skin irritation for the PD patients. In addition, intravenous administration leads to increased bioavailability compared to other forms of administration, as, for example, the gastrointestinal barrier can be bypassed.

It is preferred that the dose is administered over a period of between 45 min and 90 min, preferably about 1 h, when the composition is administered intravenously. Compared to a shorter administration period, even fewer adverse events occur when a dose is administered over this period. In the context of the present invention, the administration period of between 45 min and 90 min refers to the first dose. Even longer administration periods of between 90 min and 10 h are recommended for the second and third doses administered intravenously to avoid adverse events such as back and neck pain as well as potential pseudoallergic reactions (e.g. complement activation-related pseudoallergy (CARPA)).

In a preferred embodiment, the administration in the primary mode of administration is accompanied by administration in a secondary mode of administration in-between doses of the primary mode of administration, wherein the secondary mode of administration is preferably an oral administration. By administering additional doses in a secondary mode of administration between the doses of the primary mode of administration, the pharmacological effect is increased. For example, if the primary mode of administration is a weekly intravenous administration and the secondary mode of administration is a daily oral administration of the composition, the GM1 level in the body can be kept high. At the same time, with such an approach, the restrictions on quality of life are kept to a minimum. A subcutaneous injection of non-liposomal GM1 twice daily, as is often administered, leads to severe side effects. In comparison, an intravenous injection of liposomal GM1 once a week with additional oral doses in between, without the need for a healthcare professional to be present during oral administration, is significantly more beneficial and associated with fewer side effects for the patient. Surprisingly, despite the overall lower amount of GM1 administered and lower frequency of administration, this leads to a better pharmacological result thanks to the liposomal composition.

Preferably, the administration of the primary and/or secondary mode of administration comprises a dosing regimen of equal doses, or increasing doses of said liposomal composition comprising GM1. Possible adverse events frequently occurring in some of the first few administrations can be counterbalanced by administering smaller amounts of the liposomal composition at the earlier administrations in PD patients who experience such side effects. As soon as fewer side effects occur in a PD patient, the dose can be increased accordingly for subsequent administrations. These side effects of the liposomal composition comprise back and neck pain as well as pseudoallergic reactions (e.g. complement activation-related pseudoallergy (CARPA)) or reactions of humoral origin. It should be noted that no clinically relevant adverse events were observed with a dosing regimen corresponding to the invention.

As an alternative to administering smaller amounts of the liposomal composition to mitigate the adverse events occurring during intravenous administration, the flow rate of the infusion can be adjusted so that less liposomal composition flows into the body per unit time. Furthermore, both the amount of liposomal composition administered, and the rate of administration may be adjusted during the same administration. The choice of the amount and rate of administration depends largely on patient feedback. For example, if a patient complains of pain in the neck or/and back or/and near the injection site during administration, the amount to be administered and/or the rate of administration can be adjusted accordingly. Furthermore, the infusion can be interrupted until the symptoms of the adverse events subside.

In the context of the present invention, a dosing regimen is a schedule of doses of a therapeutic agent per unit of time including the time between doses, the amount of the therapeutic agent per dose and, in case of an intravenous injection for example, the period of time during which the dose is administered. To treat a patient, several dosing regimens of the same mode of administration can be used in succession, for example if the time between doses changes. Further, several dosage regimens can also be used in parallel, in case of different modes of administration.

Preferably, the primary mode of administration comprises a second dose of said liposomal composition comprising GM1 that is lower than the first dose and a third and subsequent doses that are increasing.

In a preferred embodiment, said composition is administered periodically every 7 days with 6 days between each administration in the primary mode of administration.

In another preferred embodiment, said therapeutically effective dose of GM1 of said liposomal composition is between 300 mg and 800 mg, preferably between 600 mg and 750 mg, most preferably about 720 mg. This dose range has been found to lead to an optimal pharmacological effect without causing severe side effects.

In a further preferred embodiment, the liposomal composition additionally comprises cholesterol, preferably sphingomyelin and cholesterol in a 1:1 molar ratio. Liposomes comprising sphingomyelin and cholesterol show an enhanced circulation lifetime and CNS bioavailability. They have improved pharmacokinetics and therapeutic characteristics. They are biocompatible and biodegradable. Although in certain cases elevated cholesterol levels may be observed after administration of the liposomal cholesterol-containing composition, these elevated cholesterol levels will return to normal levels without any resulting adverse events.

In a preferred embodiment, said therapeutically effective amount of GM1 in said liposomal composition in a single dose of the primary mode of administration is chosen such that it leads to a venous blood plasma concentration of GM1 between 50 μg/ml and 1200 μg/ml, in particular between 75 μg/ml and 600 μg/ml, further in particular between 100 μg/ml and 400 μg/ml that is reached within 1 h to 7 h, preferably within 3 h to 5 h, most preferably 4 h after the start of administration. This range of venous blood plasma concentrations of GM1 has been found to lead to an optimal pharmacological effect without causing severe side effects. It was found that with such values for a venous blood plasma concentration of GM1 that the GM1 concentration is still significantly higher compared to baseline after 96 h (see examples section hereinafter). This confirms the expectation of a long circulating drug.

In yet another preferred embodiment, the liposomes of said liposomal composition have a mean diameter between 10 nm and 70 nm, preferably between 30 nm and 70 nm, more preferably between 40 nm and 65 nm, measured by dynamic light scattering; and/or have a mean diameter between 10 nm and 50 nm, preferably between 20 nm and 50 nm, more preferably between 30 nm and 40 nm, measured by CryoTEM.

"Measured by dynamic light scattering" (DLS) means that DLS was performed on samples with a lipid concentration between 20 mg/ml and 30 mg/ml, which were diluted 1/19 in phosphate-buffered saline (PBS) or milliQ H2O to reach an attenuation factor in the instrument of around 6. DLS was measured on a Malvern Zetasizer Nano device at 25° C. and 0° scattering angle. Instrument control and data analysis were performed with the Zetasizer software (version 7.11) from Malvern. Particle size (hydrodynamic diameter) was determined using the Stokes-Einstein equation $$d(H) = \frac{kT}{3\pi\eta D}, \quad \text{Equation 1}$$

where k is the Boltzmann constant, T is the absolute temperature, $\eta$ is the dispersant viscosity and D is the diffusion coefficient. Viscosity was determined with the Zetasizer software and was 0.8872 cP. Dispersant refractive index was 1.330. D was obtained by fitting the autocorrelation function with a suitable algorithm. Cumulants analysis is a simple method of analysing the autocorrelation function generated by a DLS experiment and produces the mean particle size (Z-ave) and polydispersity index (PDI). The calculation is defined in ISO 13321 (1996) and ISO 22412 (2008). The first order result from a DLS experiment is an intensity distribution of particle sizes. The intensity distribution is naturally weighted according to the scattering intensity. The size distribution is displayed as a plot of the relative intensity of light scattered by particles (on the Y axis) versus various size classes (on the X axis) which are logarithmically spaced. Clear disposable zeta cells with a pathlength of 10 mm were used for the measurements. Usually but not necessarily, the liposomes in the inventive composition will fall into the numerical ranges of size measured by the method described.

"Measured by CryoTEM" means that the samples were subject to cryogenic transmission electron microscopy (CryoTEM). The liposomal samples diluted as appropriate, vitrified and prepared on-grid (Formvar and Carbon) with an acceleration voltage of 200 kV. Images were acquired with a CryoTEM JEOL JEM-2100F a TVIPS TemCam F415MP camera at 20'000×; 40'000×; 80'000× magnification. Particle identification and size determination were performed by semi-automated image processing using Vironova Analyzer Software, Vironova, Sweden. Briefly, a series of random images of the same magnification was imported. Only liposome particles located entirely within the boundaries of the image and with a distinct membrane were detected. The identified objects were analysed for spherical diameter, circularity, unilamellarity. All images were batch-processed with identical thresholds and settings, accumulating over 5 to 18 images for each sample, corresponding 6 to a number of particle analysed of 1560 to 1178. Mean values have a standard deviation of approx. 10 nm.

Usually but not necessarily, the liposomes in the inventive formulation will fall into the numerical ranges of size measured by both methods. The diameter size measured by CryoTEM is generally lower than the diameter size measured by DLS.

In the context of the present invention, the phrase "and/or" in relation to the measurement of the liposomal diameter is to be understood as an inclusive disjunction. This means that all liposomal compositions are included in which the liposomes usually but not necessarily fulfil either or both conditions.

It has successfully been shown that the inventive liposomes of said composition and the indicated size are more stable than those known in the art. Liposomes of such small diameter are opsonized less rapidly and at a lower extent than their larger counterparts and are cleared less rapidly by the reticuloendothelial system. Also, larger liposomes are more likely to fuse or interact with other liposomes or particles.

As a result, the serum half-life in humans of the liposomal composition according to the invention is considerably higher than the one for liposomal compositions with higher liposome diameters known in the art. Additionally, a smaller liposomal diameter allows a facilitated crossing of the blood-brain barrier. The composition thus provides higher drug exposition for a given dose in the CNS (HERSH, A. M. Crossing the Blood-Brain Barrier: Advances in Nanoparticle Technology for Drug Delivery in Neuro-Oncology. Int. J. Mol. Sci. 2022, Vol. 23, pages 1 to 28).

In a preferred embodiment, the liposomal composition comprises phosphate-buffered saline (PBS) at a pH of about 6.8, which corresponds to a physiologically well-tolerated pH.

In another preferred embodiment, the liposomal composition comprises at least one of a pharmaceutically acceptable additive, a carrier, an excipient and a diluent.

In the context of the present invention, an additive is a substance which is added in the composition along the API so as to impart specific qualities in the composition. An additive has very little or no therapeutic value but is necessary in the manufacture of a particular form of administration. An additive may serve any one of the following purposes or any combination thereof: provide bulk to the composition; facilitate drug absorption or solubility and other pharmacokinetic considerations; aid in handling of the API during manufacturing; provide stability and prevent from denaturation.

In the context of the present invention, a carrier (also known as drug carrier or drug vehicle) is a substrate used in the process of drug delivery which serves to improve the selectivity, effectiveness and/or safety of drug administration. Popular types of carriers include liposomes, micelles, microspheres and nanoparticles.

In the context of the present invention, an excipient is a substance formulated alongside the API, included for the purpose of long-term stabilization, bulking up solid formulations that contain potent active ingredients in small amounts, or to confer a therapeutic enhancement on the API, such as facilitating drug absorption, reducing viscosity or enhancing solubility or enhancing bioavailability.

In the context of the present invention, a diluent (also referred to as a filler, dilutant or thinner) is an ingredient in a medicinal preparation that lacks pharmacologic activity but is pharmaceutically necessary or desirable. It is particularly useful in increasing the bulk of potent drug substances with a mass too small for dosage to allow manufacture or administration.

In a preferred embodiment, the method of treating PD is selected from reducing tremor, increasing physical movement, increasing walking speed, improving walking ability, improving motion control, improvement of speech changes, in a patient with PD. The above complaints are common symptoms in PD patients. By treating the affected areas of the CNS with the liposomal composition according to the invention, it was found that these symptoms could be significantly reduced, when assessing the severity of the symptoms using the MDS-UPDRS system.

Another aspect of the present invention relates to a liposomal composition for use in a method of treating Parkinson's disease (PD), said liposomal composition comprising sphingomyelin in a lipid bilayer and a therapeutically effective amount of monosialotetrahexosylganglioside (GM1), wherein the treatment is an at least partial reversal of PD, and wherein the treatment optionally involves a dosing regimen with a therapeutically effective dose of said liposomal composition being administered in a primary mode of administration at most every 4 days with at least 3 days between each administration; preferably at most every 6 days with at least 5 days between each administration; most preferably at most every 7 days with at least 6 days between each administration.

In the context of the present invention, an at least partial reversal of PD is an at least partial decrease in at least one of symptoms or signs of the disease, wherein at least one of symptoms or signs do not increase substantially, compared to baseline.

It was surprisingly found that treatment of PD patients with the liposomal composition of the invention over a period of 24 weeks does not merely halt the negative development of PD, but that the symptoms and signs can be significantly reduced, even in cases where the liposomal composition of the invention is administered at 7-day intervals.

The invention will be further explained by the following examples. The examples are not intended to limit the scope of the invention in any way.

The preparation of the liposomal composition containing GM1 is disclosed herein. In particular, the circularity of the liposomes used for the liposomal composition of the present invention is greater than or equal to 0.95, in particular 0.98-1.00.

The liposomal composition comprising GM1 used for the intravenous administration in the following examples may hereinafter be called "TLN" or "Talineuren".

The invention will be further outlined in the following:

FIG. 1: In vivo biodistribution of liposomes comprising sphingomyelin labelled with ICG according to the invention.

Figure 2:
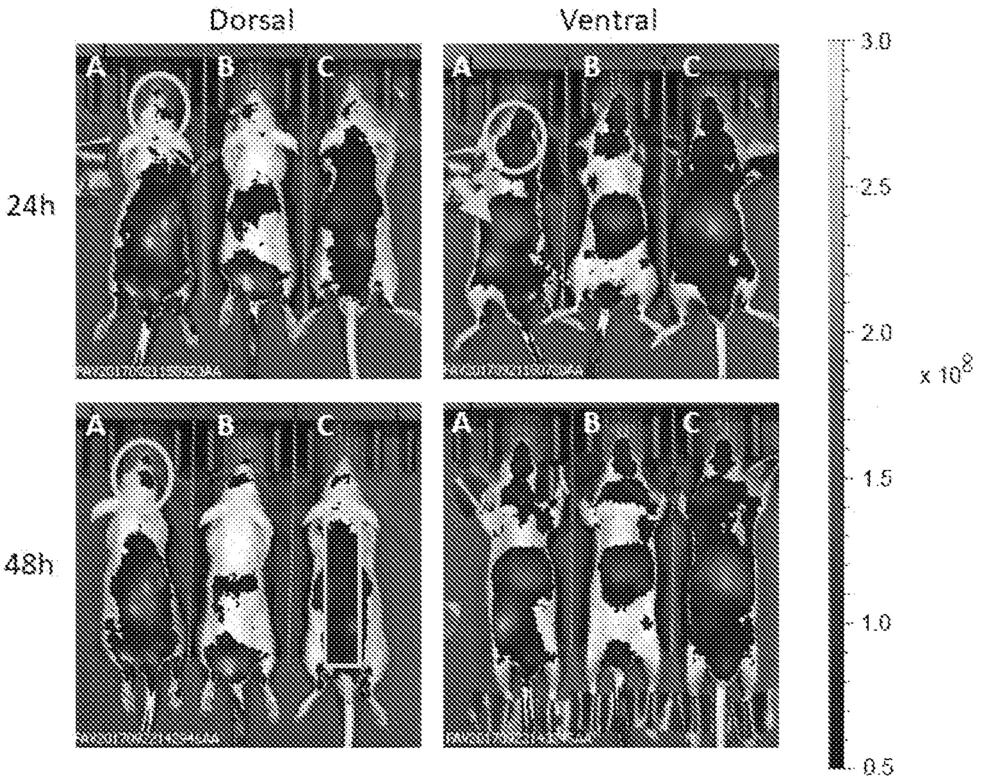

FIG. 2: In vivo biodistribution of liposomes comprising sphingomyelin labelled with DiR according to the invention.

Figure 3:
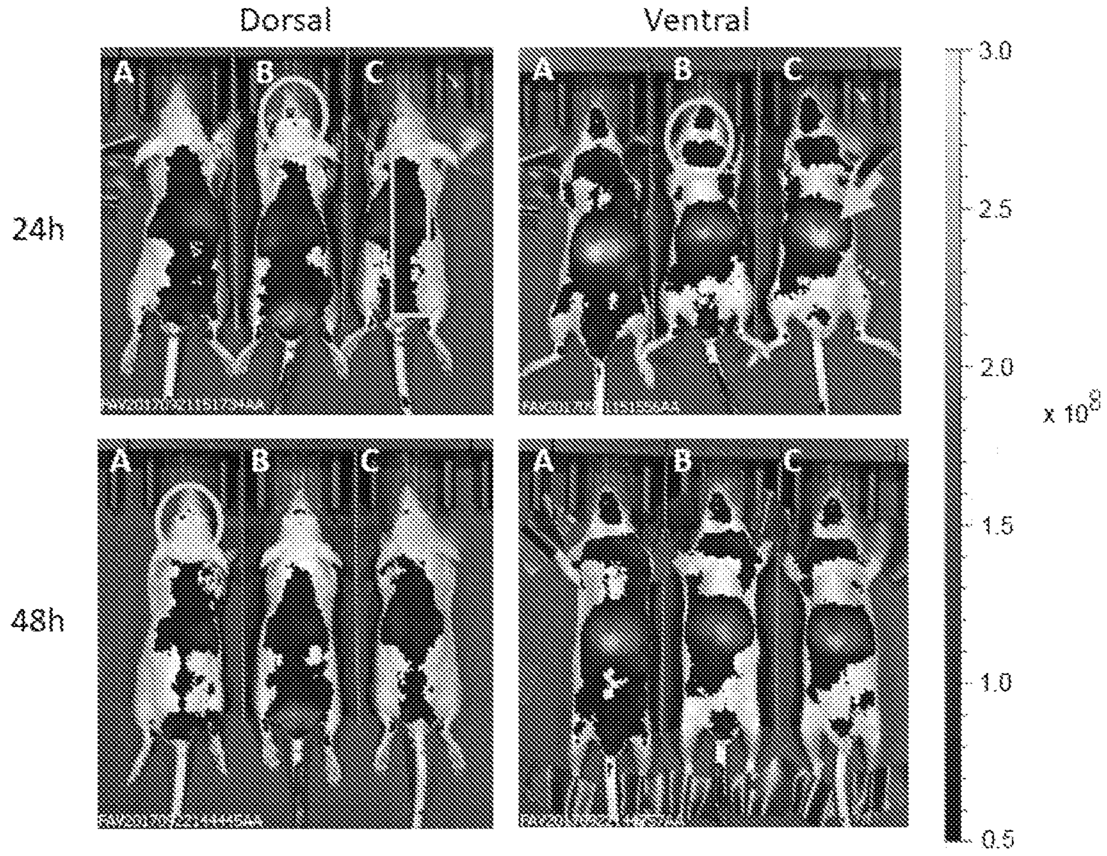

FIG. 3: In vivo biodistribution of liposomes comprising sphingomyelin and GM1 labelled with DiR as comparative example to FIG. 2.

FIG. 4: Graphic representation of the biodistribution analysis in the brain, spinal cord, liver and spleen from the in vivo biodistribution images of FIGS. 2 and 3.

Figure 5:
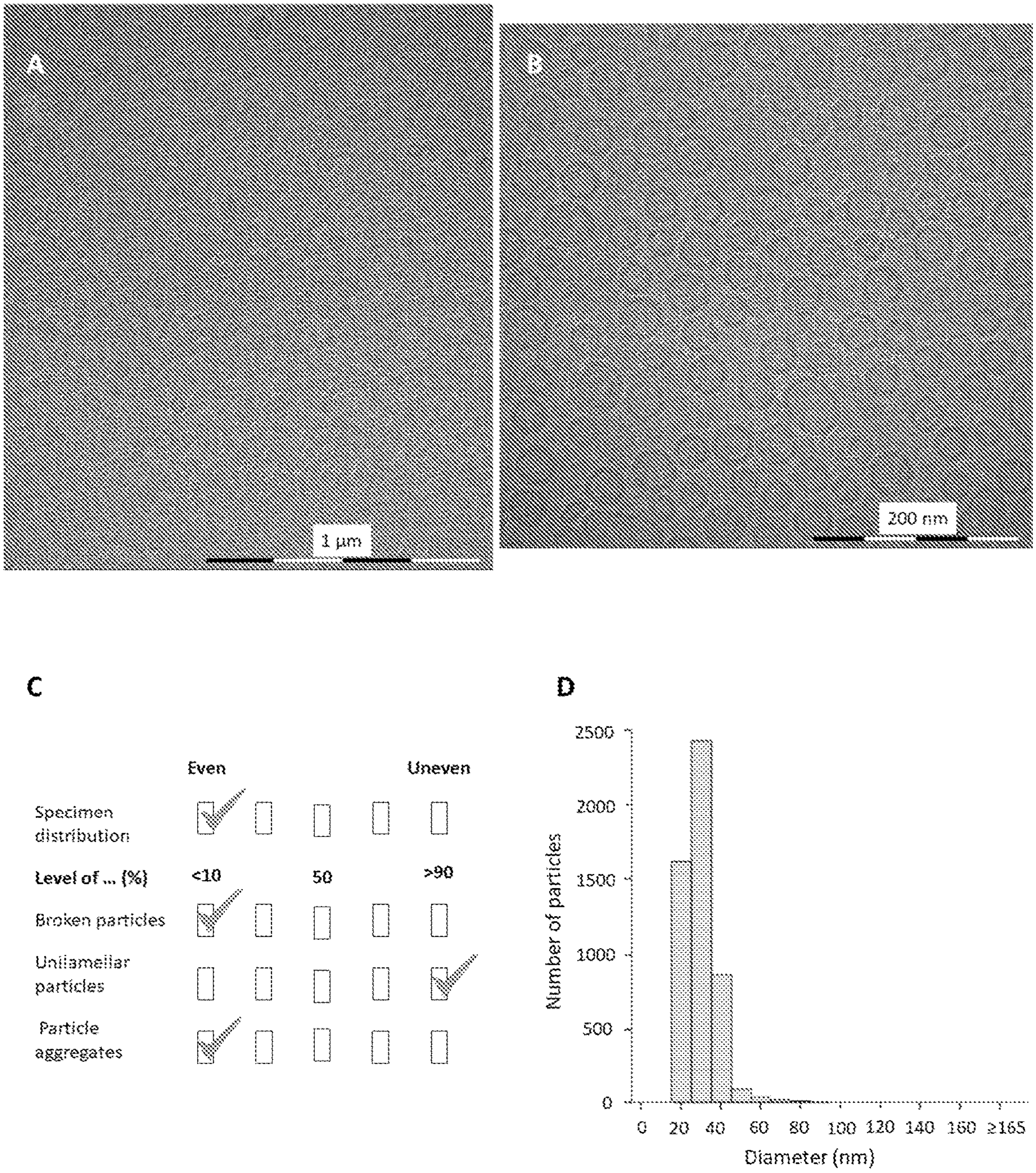

FIG. 5: Characterization of the liposomes without surface modification by cryoTEM: (A) Visualization low magnification, (B) Visualization high magnification, (C) Qualitative assessment, (D) Quantitative diameter distribution.

Figure 6:
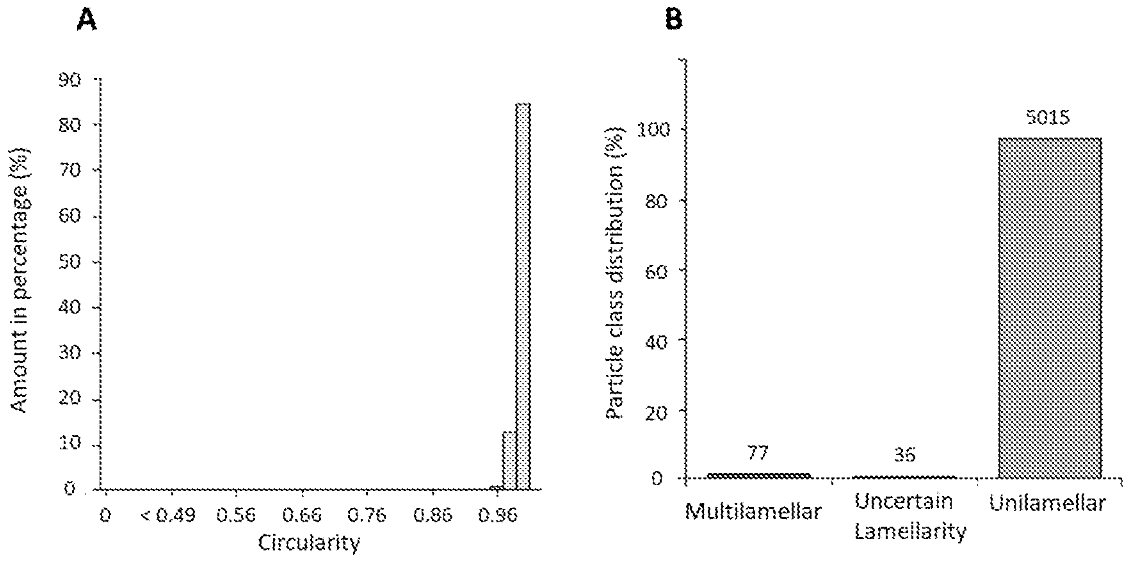

FIG. 6: Quantitative characterisation of the liposomes without surface modification by cryoTEM. (A) circularity distribution, (B) lamellarity diagram.

FIG. 7: Characterization of size stability of the liposomes over time, measured by dynamic light scattering DSC.

FIG. 8: Characterization of polydispersity stability of the liposomes over time, measured by dynamic light scattering DSC.

Figure 9:
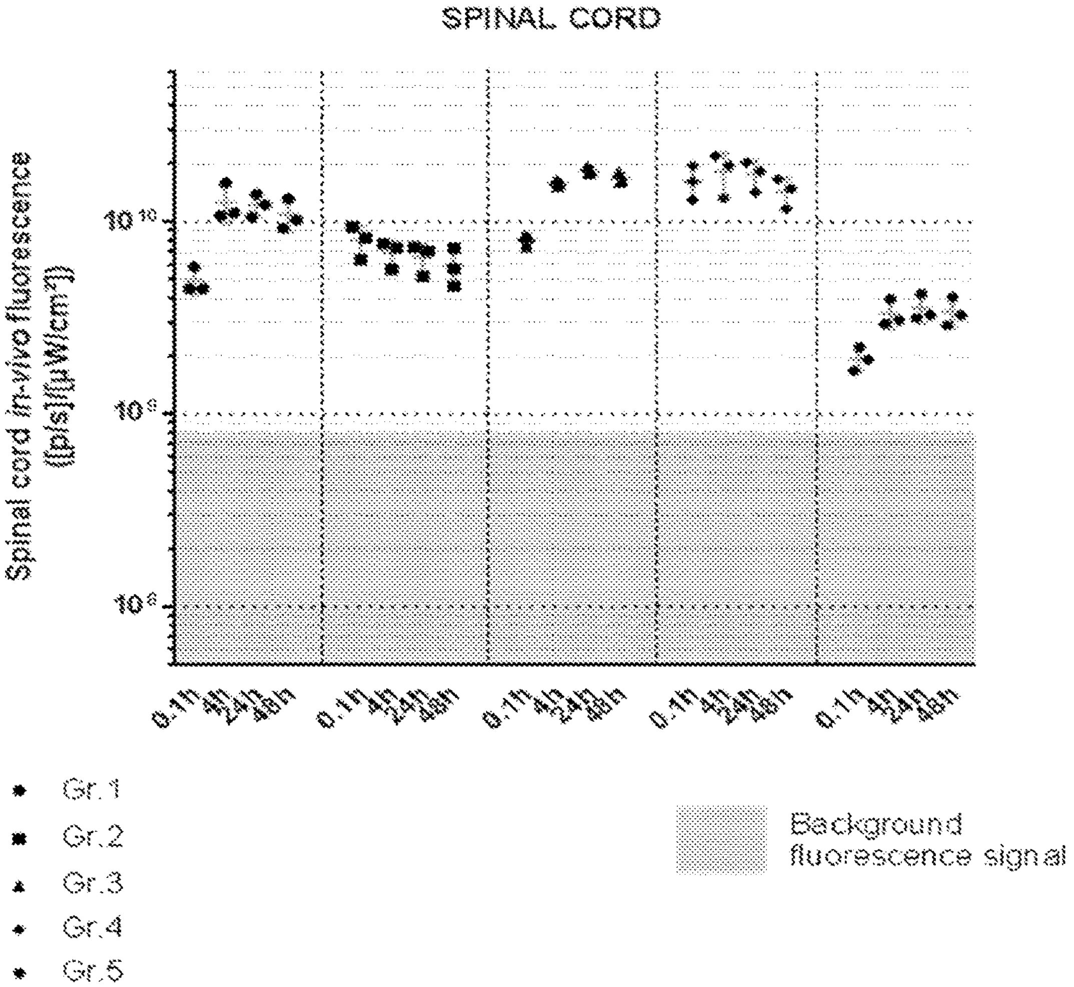

FIGS. 9/10: In-vivo fluorescence of different liposomal formulations in spinal cord and brain.

Figure 11:
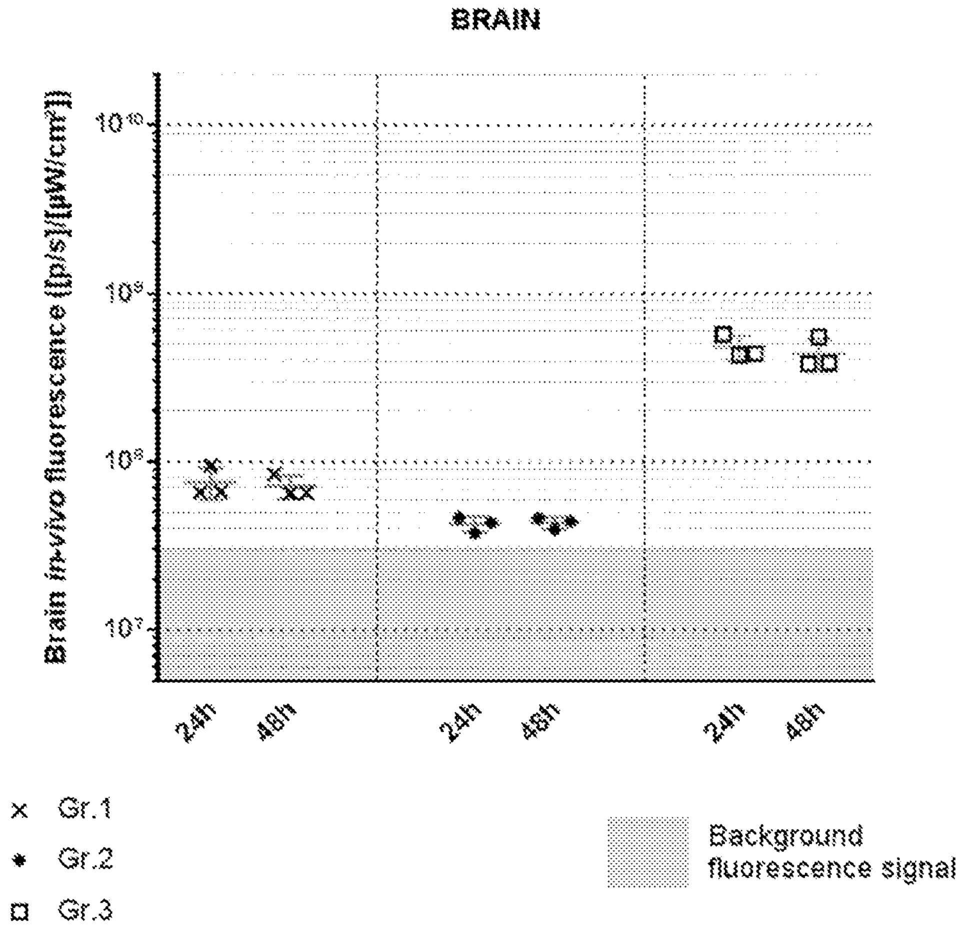
Figure 13:
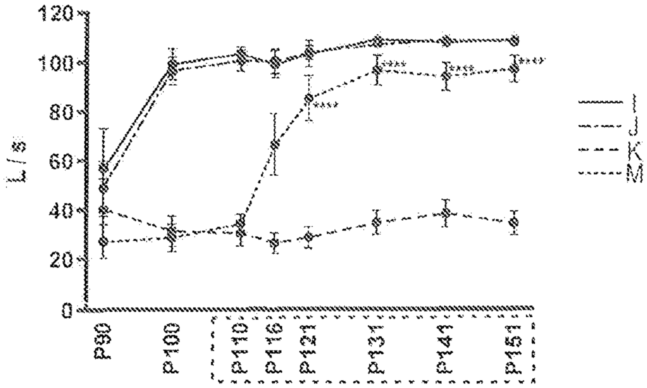
Figure 14:
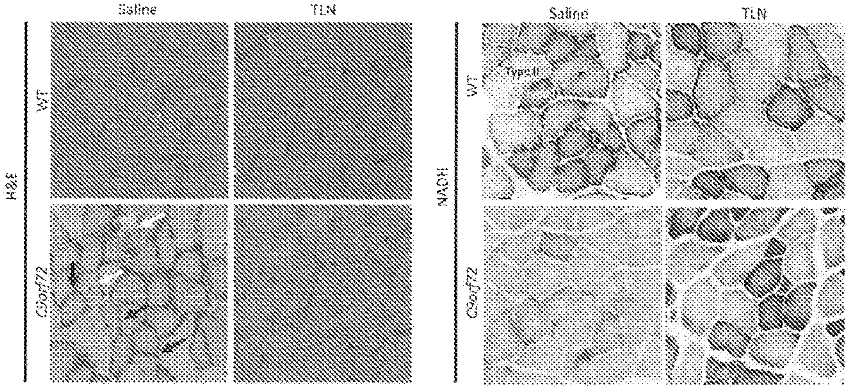
Figure 15:
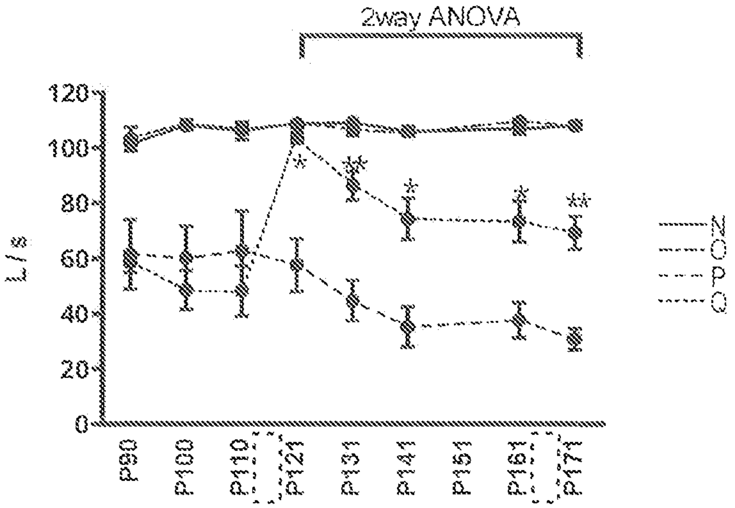
Figure 16A:
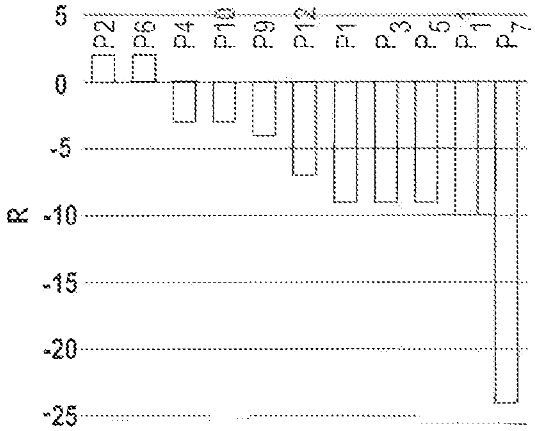
Figure 17A:
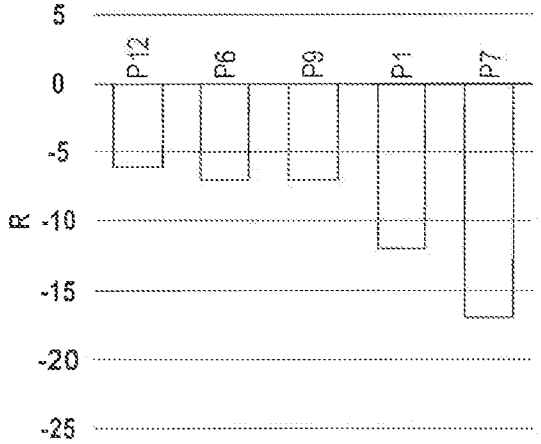
Figure 18:
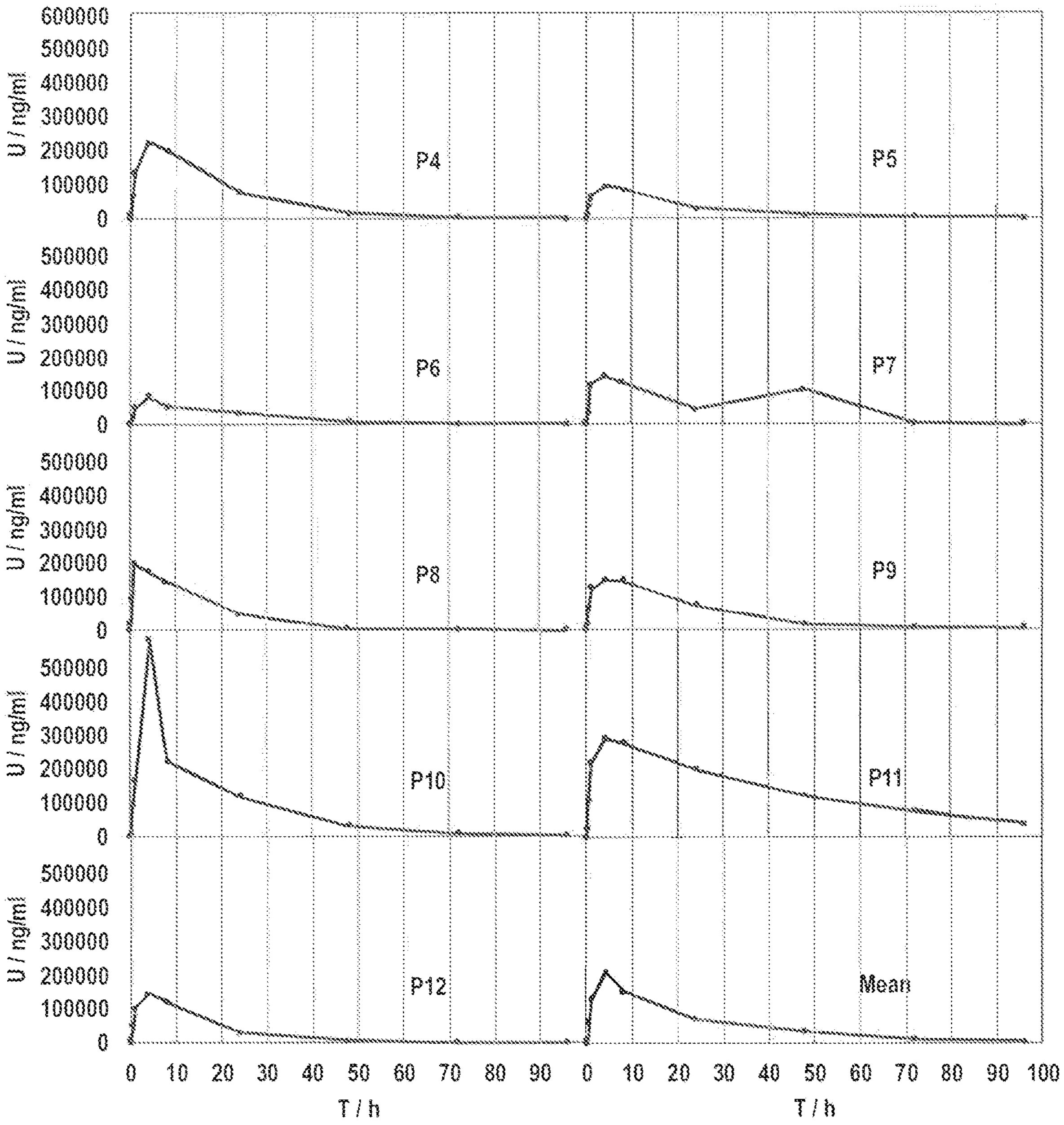

FIG. 11: In-vivo fluorescence of liposomal formulations with different lipid compositions in the brain FIG. 12*a*-12*c*: striatal levels of dopamine and its metabolites in mice of the MPTP-PD model: levels of dopamine (DA, FIG. 1*a*), 3,2-dihydroxyphenylacetic acid (DOPAC, FIG. 1*b*) and homovanillic acid (HVA, FIG. 1*c*) determined by HPLC, n=5-10, bars indicate means and standard deviation, one-way ANOVA treatment groups p-value *<0.05, **<0.01;

FIG. 13: reverse rotarod test performance of C9orf72 mice: reverse rotarod test with treatment initiation at P110 until P151 (15 mg/kg saline or Talineuren (TLN), intravenous administration, every other day, dotted box), n=5-7/grp. Values represent means and standard error of means. Differences were assessed using 2way ANOVA with Bonferroni's multiple comparisons test, ****p<0.0001;

FIG. 14: hematoxylin and eosin (H&E) and NADH staining of the gastrocnemius muscle of C9orf72 mice at P170. Left: H&E staining of the gastrocnemius muscle. The black arrows show angular fibres. The white arrows indicate muscle fibres with a central nucleus indicative of denervation. Right: NADH staining showing Type I (dark) and Type II (light) myofibers. n=3 animals/grp. Samples were stained and imaged with the same settings;

FIG. 15: reverse rotarod test performance of SOD1-G93A mice, with treatment initiation at P110 to P121 and P160 to P170 (15 mg/kg saline or Talineuren ganglioside (TLN), intravenous administration, every other day, dotted boxes), n=4-6/grp. Values represent means and standard error of means. Differences were assessed using 2way ANOVA with Bonferroni's multiple comparisons test, ****p<0.0001;

FIG. 16*a*+16*b*: difference in MDS-UPDRS motor (FIG. 5*a*) and total (FIG. 5*b*) score for each patient (P1-P7; P9-P12) between baseline and assessment after 8 weeks of treatment. 5a: change in UPDRS motor score ("off" standard medication for 12 h) (R); 5b: change in UPDRS total score (S);

FIG. 17*a*+17*b*: difference in MDS-UPDRS motor (FIG. 6*a*) and total (FIG. 6*b*) score for each patient (P1; P6; P7; P9; P12) between baseline and assessment after 24 weeks. 6a: change in UPDRS motor score ("off" standard medication for 12 h) (R); 6b: change in UPDRS total score (S);

FIG. 18: GM1 concentration (U) over time (T) in the blood plasma for all nine patients in the dose consolidation group and the mean value of each measured point in time;

FIG. 19*a*+19*b*: TLN-DiI uptake in cells of the mouse brain: 8a: substantia nigra after 48 h (TLN-DiI, i.v., 30 mg/kg). DAPI (nuclear DNA, blue), DiI (dye, red). 8b: motor cortex after 24 h (TLN-DiI, i.v., 15 mg/kg) Scale bar=50 μm, white arrows indicate DiI-positive cells;

FIG. 20: GM1 levels in the rat brain (V) determined by LC-MS/MS after 12.3 mg/kg bodyweight administration of GM1 (free or in form of Talineuren) intravenously once daily. (t-test with welch correction, p-value<0.05), bars indicate mean and standard deviation, n=5.

FIG. 1 shows the in vivo biodistribution of sphingomyelin liposomes labelled with Indocyaninegreen (ICG). Mice were treated intravenously with liposomes carrying near-infrared dye and biodistribution was analysed 24 hours post-injection. Analysis was performed with a GE HealthCare eXplore Optix. Signals of the ICG were found in brain (A) and the spinal cord (B). Total liposome lipid injection was 45 mg/kg carrying 1:200 weight-to-weight ICG. Further signals could be found in the clearance organs liver (C) and spleen (D), indicating that after treatment the liposomes can be removed from the body.

FIG. 2 shows the in vivo biodistribution of sphingomyelin liposomes labelled with DiR. Different mice A, B, C were treated intravenously with liposomes carrying near-infrared dye and biodistribution was analysed 24 and 48 hours post-injection in a ventral view and a dorsal view. Analysis was performed with an optical imaging system, IVIS Spectrum of Perkin Elmer. Signals of the DiR were found in the brain (circle) and spinal cord (rectangle). Total liposome lipid injection was 15 mg/kg carrying 50 μg/ml DiR. Further signals could be found in the clearance organs liver (plain arrow) and spleen (doted arrow), indicating that after treatment the liposomes can be removed from the body. The fluorescence scale is termed in the following unit: total Radiant efficiency [p/s]/[μW/$cm^2$].

FIG. 3 shows a comparative example of the in vivo biodistribution of a liposome with sphingomyelin and GM1, labelled with DiR. Mice were treated intravenously with liposomes carrying near-infrared dye and biodistribution was analysed 24 and 48 hours post-injection. Analysis was performed with an optical imaging system, IVIS Spectrum of Perkin Elmer. Signals of the DiR were found in brain (circle) and the spinal cord (rectangle). Total liposome lipid injection was 25 mg/kg carrying 50 μg/ml DiR. Further signals could be found in the clearance organs liver (plain arrow) and spleen (doted arrow), indicating that after treatment the liposomes can be removed from the body. The fluorescence scale is termed in the following unit: total Radiant efficiency [p/s]/[μW/$cm^2$]. Even though the liposomes are found in the same organs as the liposomes presented in FIG. 2, the biodistribution is less distinct compared to the essentially GM1-free liposomes in FIG. 2.

FIG. 4 shows a graphic representation of the biodistribution analysis in the brain, spinal cord, liver and spleen from the in vivo biodistribution images of FIG. 2 and FIG. 3. FIG. 4A shows the normalised fluorescence of the biodistribution of the liposome without ganglioside in four different tissues: brain, spinal cord, liver and spleen. The biodistribution is displayed for two different time points: 24 and 48 hours. The bars represent the standard deviation to the mean. FIG. 4B shows the normalised fluorescence of the biodistribution of the liposome with ganglioside.

It was surprisingly found, that the in vivo biodistribution of the liposome essentially lacking ganglioside (FIG. 4A) is higher than the in vivo biodistribution of the liposome comprising ganglioside (FIG. 4B).

FIG. 5 shows the characterization of the liposomes without surface modification. liposomes were visualized using Cryo Transmission Electron Microscope JEOL JEM-2100F and a TVIPS Tem-Cam camera (JEOL Ltd., Japan). FIG. 5A shows an image of the liposomes at low magnification (20000×). FIG. 5B shows the liposomes at high magnification (80000×). FIG. 5C shows a qualitative assessment done by ocular/visual observation of the liposomal distribution. FIG. 5D shows the size distribution of the liposomes of this invention. In order to quantify the mean diameter of the liposomes N(liposomes)=5128 were analysed (Vironova Analyzer Software, Vironova, Sweden). The mean diameter of the liposomes is 30.46 nm with a standard deviation of 10.10 nm.

FIG. 6 comprises two further tests for a quantitative characterisation of the liposomes without surface modification by cryoTEM (Vironova Analyzer Software, Vironova, Sweden). FIG. 6A shows the circularity distribution of 5128 liposomes. FIG. 6B shows the lamellarity grade of the liposomal distribution. 98% of 5128 liposomes have been characterised as unilamellar.

FIGS. 7 and 8 show the size and polydispersity stability of liposomes according to the invention over time, measured by dynamic light scattering. The liposomal formulations were obtained according to the method described above, by using sphingomyelin and cholesterol in a 1:1 molar ratio. The liposomes were completely free of gangliosides, surface modifications, and did not comprise or encapsulate an active component. The liposomal formulations were stored in PBS at a pH-value of 6.8 and a temperature of 4° C. Size and polydispersity were determined by DLS standard methods. It shall be noted that the values measured by dynamic light scattering are slightly higher than the values obtainable by cryoTEM due to the impact of the hydrodynamic radius of liposomes on DLS measurements. A diameter of 60 nm as indicated in FIG. 7 corresponds to a mean diameter in the range of 10 and 50 nm when measured by Cryo Transmission Electron Microscopy.

The dotted curve shows the results of a small scale production batch of liposomal formulation as described above, while the dashed curve shows the results of an upscale production, i.e. a batch size of 2 litres. As can be seen from FIGS. 7 and 8, both the size and polydispersity of the liposomal formulations from Q3 2017 to Q3 2018, i.e. during storage time of one year, remained essentially unchanged.

Figure 10:
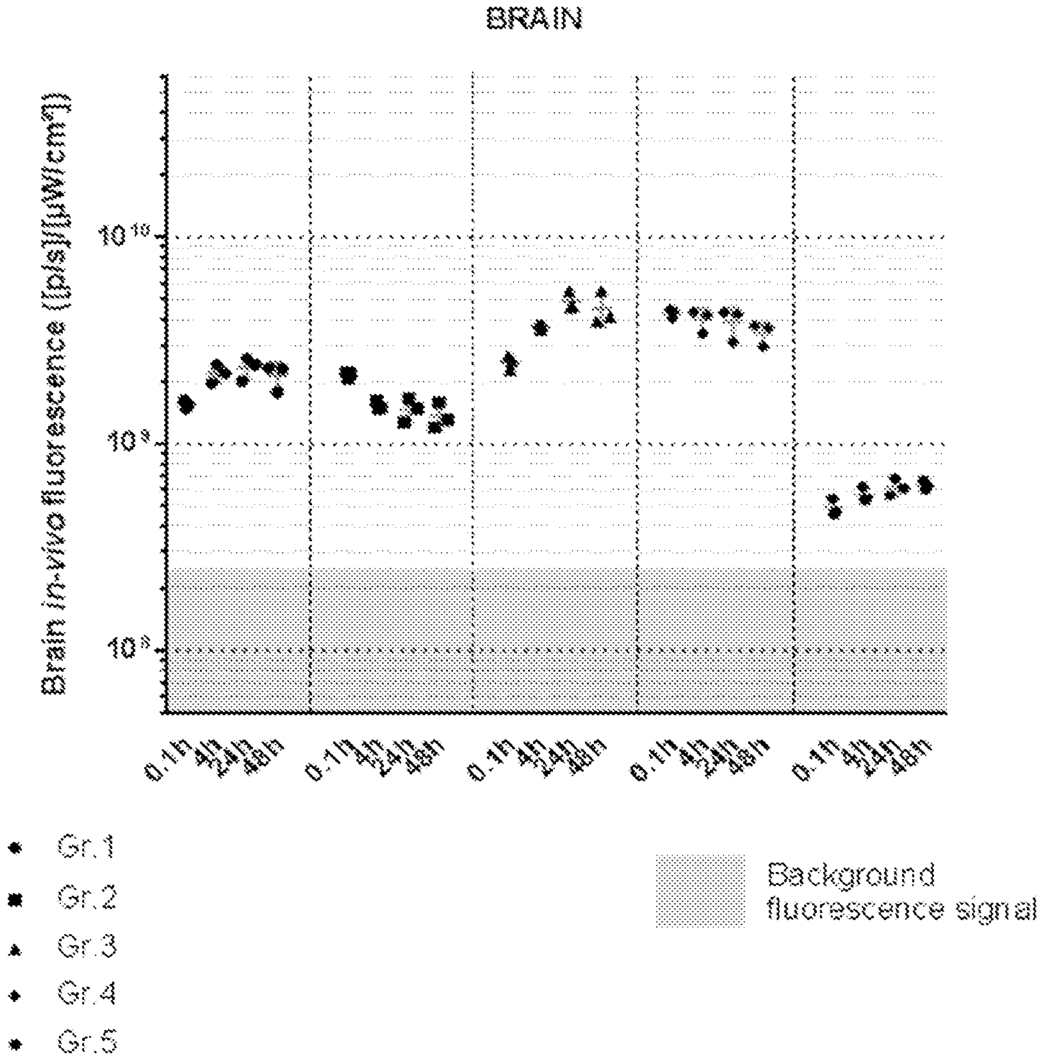

FIGS. 9 and 10 show relative in-vivo fluorescence of different liposomal formulations in the spinal cord and brain of mice. In both charts, the liposomes of groups 1 to 4 were obtained according to the method described above, by using only sphingomyelin and cholesterol in a 1:1 molar ratio. Gr. 5 is a control group of free DiR in PBS. In Gr.1, synthetic sphingomyelin was used and GM1 was comprised in the liposomes. In Gr. 2, synthetic sphingomyelin was used and the liposome was completely free from surface modifications, in particular free from GM1. In Gr. 3, sphingomyelin of animal origin was used and GM1 was comprised in the liposomes. In Gr. 4 sphingomyelin of animal origin was used and the liposome was completely free from surface modifications, in particular free from GM1. For all four test groups, DiR was added as a labelling agent. The measurements were performed by NIR imaging technique.

FIGS. 9 and 10 show the accumulation of the four different kinds of liposomes in the spinal cord and brain respectively in 0.1 h, 4 h, 24 h and 48 h post-injection. It can be seen that the presence of GM1 does not significantly affect the ability of the liposomes to target the central nervous system. The same holds true for the use of synthetic sphingomyelin compared to the use of sphingomyelin of animal origin.

FIG. 11 shows the relative in-vivo fluorescence of liposomal formulations with different lipid compositions in the brain of mice. The liposomes of groups 1 to 3 were obtained according to the method described above by using lipids and cholesterol in a 1:1 molar ratio. In group 1, phosphatidylcholine and sphingomyelin in combination were used as lipids. In group 2, phosphatidylcholine alone was used as a lipid. In group 3, sphingomyelin alone was used as a lipid. In all three test groups, DiR was added to the formulations as a labelling agent. The measurements were performed by NIR imaging technique.

FIG. 11 shows the accumulation of the three different kinds of liposomes in the brain of mice after 24 h and 48 h post-injection. It can be seen that the composition consisting of sphingomyelin and cholesterol alone results in superior longevity of circulation and CNS bioavailability of the liposome compared to the other variants (Grps 1 and 2).

Talineuren has been investigated in a number of preclinical models of neurological diseases. Efficacy studies have been conducted in animal models of different movement disorders, such as the MPTP-mouse model of PD, the C9orf72 and Sod1 mouse model for amyotrophic lateral sclerosis.

Example 1: Talineuren in Models of PD

MPTP (1-methyl-4-phenyl-1,2,3,6-tetrahydrophyridine) is a prodrug to the neurotoxin $MPP^+$, which causes permanent symptoms of PD by destroying dopaminergic neurons in the substantia nigra of the brain.

Studies in the MPTP-mouse model of PD, where the dopaminergic neurodegeneration is induced by a neurotoxin produced mixed results. MPTP was given twice a day at the dose of 20 mg/kg in saline i.p. (intraperitonial) at 4 h intervals on two consecutive days (Days 1 and 2), the total amount being then 80 mg/kg. Dosing volume for MPTP was 10 mL/kg and pure MPTP active compound concentration was 1.6 mg/mL (after salt correction factor had been reduced). MPTP dosing was started in the morning (8-9 AM).

Mice received Talineuren, p.o. (per os; orally) daily for 14 days (Days 1-14). The dosing volume was 5 ml/kg. On MPTP dosing days (Days 1-2) the compound dosing was performed on the evening (6-8 PM). On Day 3 the compound dosing was performed on afternoon (1-2 PM). On Days 4-14 the compound dosing was performed starting 7 AM.

Figure 12A:
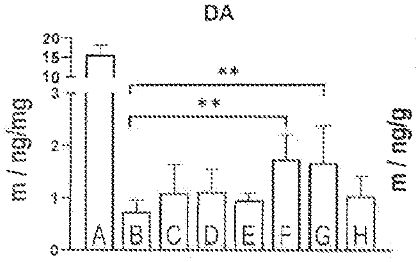
Figure 12B:
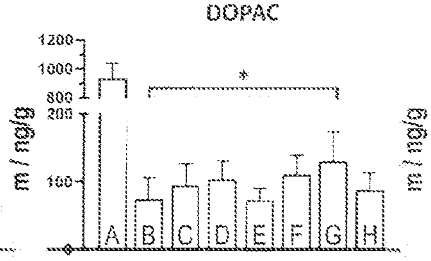
Figure 12C:
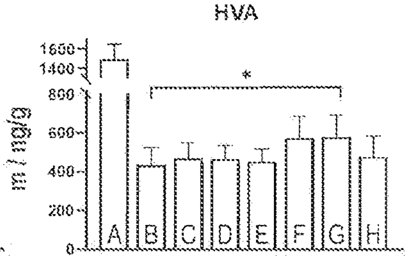

FIG. 12 shows the striatal levels of dopamine (DA, FIG. 12*a*), 3,2-dihydroxyphenylacetic acid (DOPAC, FIG. 12*b*) and homovanillic acid (HVA, FIG. 12*c*) determined by high-performance liquid chromatography (HPLC). 5-10 subjects were examined for each treatment group and the bars indicate means and standard deviation in the wet tissue. The groups received the following treatments:

A: Sham;
B: MPTP+PBS;
C: MPTP+BV (base vesicle) 30 mg/kg, p.o.;
D: MPTP+GM1 30 mg/kg, i.p.;
E: MPTP+GM1 30 mg/kg, p.o.;
F: MPTP+TLN 7.5 mg/kg, p.o.;
G: MPTP+TLN 15 mg/kg, p.o.; and
H: MPTP+TLN 30 mg/kg, p.o.

In the first study with oral administration of 7.5 mg/kg (F) and 15 mg/kg (G) Talineuren showed partial rescue of dopamine and dopamine metabolite levels in the substantia nigra.

Example 2: Talineuren in Models of ALS

Amyotrophic lateral sclerosis (ALS) is a progressive nervous system disease that affects nerve cells in the brain and spinal cord, causing loss of muscle control.

To evaluate a potential therapeutic effect in ALS, two preclinical models with the most frequent mutations in familial ALS were used. In the C9orf72 and SOD1 mouse model for amyotrophic lateral sclerosis Talineuren ganglioside improved motor performance of mice and reduced ER stress on a cellular level. The liposomes uptake was shown on in vitro cultures of cortical neurons in culture but also in motoneurons of the spinal cord in vivo. More importantly, Talineuren ganglioside treatment in the C9orf72 transgene model of ALS showed a remarkable effect on motor performance. Motor function and coordination were significantly improved not only upon intravenous Talineuren treatment initiation at an early stage of the disease but also when started at a more advanced stage.

FIG. 13 shows the reverse rotarod test performance of C9orf72 mice. The test is used to assess motor coordination and balance in rodents. The apparatus consists of a motorized, circular rod turning at a constant or increasing speed. Rodents naturally try to stay on the rotarod to avoid falling on the platform. The latency to fall (L) is measured in seconds. FIG. 13 shows the following curves:

I: wildtype mice injected with saline only;
J: wildtype mice injected with Talineuren;
K: C9orf72-mice injected with saline only;
M: C9orf72-mice injected with Talineuren.

The treatment was initiated at postnatal day 110 (P110) until P151 (dotted box in FIG. 2). When intravenous treatment was initiated at the early stage of the disease and continued, prolonged latency to fall (L) at nearly wildtype (WT) level was observed in the C9orf72-mice injected with Talineuren (M). The high latency to fall (L) was sustained until the end of treatment at P151. Throughout the treatment period, this effect remained highly significant. In the hanging wire test performed at postnatal day 140 (P140) muscular strength was also improved in the C9orf72 mice treated with Talineuren ganglioside compared to the C9orf72 saline group.

These changes in the physical condition of the mice were supported by microscopic observation on sections of the spinal cord (FIG. 14). Talineuren ganglioside treatment mitigated metabolic stress as shown by downregulation of markers for Endoplasmic Reticulum stress (BiP: glucose-regulated protein), which is known to be involved in ALS progression.

Neuronal inclusions of PolyGA, a protein translated from the repeat expansion in the C9orf72 mutation, are abundant in patients with ALS and detected in post-mortem tissues. PolyGA aggregation is correlated with the unfolded protein response and triggers behavioural deficits through inflammation and protein sequestration that likely contribute to the prodromal symptoms and disease progression of C9orf72 patients (SCHLUDI, M. H. et al. Spinal poly-GA inclusions in a C9orf72 mouse model trigger motor deficits and inflammation without neuron loss. Acta Neuropathol. 2017, Vol. 134, No. 2, pages 241 to 254). In the Talineuren-treated animals, there is a significant reduction of the large PolyGA aggregates. In the skeletal muscle, denervation of the neuromuscular junctions of mice carrying the C9orf72 mutation has been previously described (LIU, Y. et al. C9orf72 BAC Mouse Model with Motor Deficits and Neurodegenerative Features of ALS/FTD. Neuron 2016, Vol. 90, No. 3, pages 521 to 534). In preclinical testing, H&E staining of the gastrocnemius muscle at P170 revealed groups of angular fibres and muscle fibres with central nucleus indicative of muscle fibre degeneration and denervation in C9orf72 untreated mice but not in WT mice or C9orf72 mice treated with Talineuren (see panels on the left of FIG. 14). In additional, nicotinamide adenine dinucleotide (NADH) staining showed Type I and II myofibers in WT mice. The myofibrillar architecture was reduced in untreated C9orf72 mice, indicating mitochondrial or sarcoplasmic reticulum abnormalities and neurogenic process (see panels on the right of FIG. 14). C9orf72 animals that received Talineuren showed almost WT characteristics.

The therapeutic effect of intravenously administered Talineuren was also observed in the preclinical ALS model with the SOD1 mutation. FIG. 15 shows the following curves:

N: wildtype mice injected with saline only;

O: wildtype mice injected with Talineuren;

P: C9orf72-mice injected with saline only;

Q: C9orf72-mice injected with Talineuren.

Two treatment intervals between P110 and P121 as well as between P161 and P171 are marked with dotted boxes in FIG. 15. Ten days of treatment starting at postnatal day P110 resulted in improved rotarod performance of the animals carrying the mutation. Although the effect was diminished over time, animals that received the treatment sustained improved performance. A second treatment interval at P160 could not enhance performance, however.

Example 3: Clinical Trial Results

A phase I clinical trial has been conducted as an open-label, single ascending dose escalation (n=3) followed by a multiple administration dose at the maximal suitable dose (n=9) (Neurologisches Institut Konolfingen; ClinicalTrials-.gov identifier: NCT04976127). The primary objective was to demonstrate the safety of TLN administration intravenously in Parkinson's patients. Secondary objectives were the determination of the maximal suitable dose based on the safety profile and preliminary efficacy, as well as the determination of the pharmacokinetics profile.

Dose Escalation

The administered dose in all three PD patients was increased on a weekly basis up to the maximal intended dose of 720 mg without any serious adverse events nor dose delays or dose modifications. Thus, the maximal suitable dose for the dose consolidation part of the trial was determined at the highest dose-level (720 mg). This confirms the expected good tolerability of the drug.

Dose Consolidation

Nine additional patients were enrolled in the trial and treated at this established therapy dose for a period of eight weeks. All 9 patients have completed the Talineuren treatment with a duration of 8 weeks. Pharmacokinetic blood samples measuring GM1 in serum were taken at 10 different time points during the first day of Talineuren administration and the following days. All samples were analysed and the results are presented below.

Optional Prolongation of Treatment

All patients already enrolled into the trial expressed the wish to continue with weekly Talineuren treatment, as they subjectively experienced benefits from the treatment. As Talineuren is generally well tolerated, the trial was extended twice (prolongation 1:8 weeks; prolongation 2:16 weeks). This allowed the continuation of an eventual benefit from Talineuren for the patients whilst gathering further safety data on the investigational medicinal product from repeated dosing with 720 mg.

Safety/Tolerability

Treatment is generally well tolerated and no serious adverse events have occurred. Several patients experienced CARPA (complement-activation related pseudoallergy; patients experienced neck pain and headache that rapidly stopped with the reduction of the speed of the infusion) which are according to the safety definitions of the Clinical Trial Protocol not judged as serious adverse events. CARPA is a known phenomenon in nanotechnological investigational medicinal products, and all CARPAs experienced in this study were fully reversible.

Efficacy after 8 Weeks of Treatment

The efficacy analysis after 8 weeks of treatment contains data from all patients that were treated for the full study period of 8 weeks of treatment with weekly infusions of 720 mg of the active pharmaceutical ingredient GM1 ganglioside in the liposomal formulation of the invention (11 out of 12 patients). One patient (Patient no. 8) only received the treatment for two weeks and dropped out of the study.

For efficacy measurement, two evaluations were considered:

1) The MDS-UPDRS motor score (part III). Following the literature (SCHNEIDER, J. S. et al. A Randomized, Controlled, Delayed Start Trial of GM1 Ganglioside in Treated Parkinson's Disease Patients. J. Neurol. Sci. 2013, Vol. 324, No. 1, pages 140 to 148), the evaluation was performed in an "off" medication state, meaning that the patients were put off their standard treatment for 12 hours. The evaluation was performed at two timepoints: the first being the baseline (BL) measurement before treatment start, the second being one week after the final treatment during the final assessment (FA) after 8 weeks.
2) The MDS-UPDRS total score. Part III was measured as described in 1). Parts I, II and IV correspond to the standard evaluation procedure of MDS-UPDRS using questionnaires. The evaluations were performed during the first Talineuren treatment (BL) and one week after the last treatment (FA).

Table 1 shows the data points for each patient separately according to the trial database for both considered efficacy measures (motor score in the "off" state and MDS-UPDRS total score). Columns three and six show the difference between the baseline (BL) assessment and the final assessment (FA) after 8 weeks for each patient. The motor score was on average reduced by 6.73 points and the total score by 12.09 points, respectively. Using a Wilcoxon rank sign test for non-parametric, paired samples, the differences are statistically significant at the 1% level. Clinically, the difference is also considered relevant since the "minimally clinically important difference" (MCID) according to literature is an improvement by about 4.3 to 5 points.

TABLE 1

| | Part III: Motor Score | | | MDS-UPDRS Total Score | | |
|---|---|---|---|---|---|---|
| | BL off | FA off | Difference | Total BL | Total FA | Difference |
| Patient 1 | 17 | 8 | −9 | 36 | 18 | −18 |
| Patient 2 | 8 | 10 | 2 | 16 | 12 | −4 |
| Patient 3 | 10 | 1 | −9 | 25 | 14 | −11 |
| Patient 4 | 6 | 3 | −3 | 10 | 5 | −5 |
| Patient 5 | 17 | 8 | −9 | 29 | 13 | −16 |
| Patient 6 | 17 | 19 | 2 | 51 | 51 | 0 |
| Patient 7 | 36 | 12 | −24 | 88 | 57 | −31 |
| Patient 9 | 22 | 18 | −4 | 28 | 24 | −4 |
| Patient 10 | 9 | 6 | −3 | 19 | 15 | −4 |
| Patient 11 | 17 | 7 | −10 | 41 | 16 | −25 |
| Patient 12 | 18 | 11 | −7 | 32 | 17 | −15 |
| Mean | 16.09 | 9.36 | −6.73 | 34.09 | 22.00 | −12.09 |

Figure 16B:
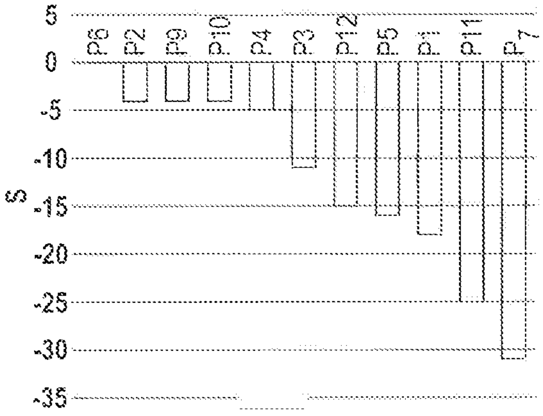

FIG. 16*a* and FIG. 16*b* show the difference between the baseline (BL) and the final assessment (FA) after 8 weeks of the MDS-UPDRS motor score (part III) and the MDS-UPDRS total score, respectively, for each patient (P1-P7; P9-P12) in descending order. The labels on the Y-axis mean:

R: change in UPDRS motor score ("off" standard medication for 12 h);

S: change in UPDRS total score.

Efficacy after 24 Weeks of Treatment

Due to the promising results after 8 weeks of treatment, the treatment was continued up to a total treatment period of 24 weeks. Data for patients P1, P6, P7, P9 and P12 were available at the filing date. The efficacy analysis after 24 weeks of treatment contains data from these five patients that received weekly infusions of 720 mg of the active pharmaceutical ingredient GM1 ganglioside in the liposomal formulation of the invention.

TABLE 2

| | Part III: Motor Score | | | MDS-UPDRS Total Score | | |
|---|---|---|---|---|---|---|
| | BL off | FA off | Difference | Total BL | Total FA | Difference |
| Patient 1 | 17 | 5 | −12 | 36 | 16 | −20 |
| Patient 6 | 17 | 10 | −7 | 51 | 46 | −5 |
| Patient 7 | 36 | 19 | −17 | 88 | 60 | −28 |
| Patient 9 | 22 | 15 | −7 | 28 | 19 | −9 |
| Patient 12 | 18 | 12 | −6 | 32 | 19 | −13 |
| Mean | 16.09 | 12.20 | −3.89 | 34.09 | 32.00 | −2.09 |

Table 2 shows the data points for patients P1, P6, P7, P9 and P12 for both considered efficacy measures (motor score in the "off" state and MDS-UPDRS total score). Columns three and six show the difference between the baseline (BL) assessment and the final assessment (FA) after 24 weeks for each patient. The motor score was on average reduced by 3.89 points and the total score by 2.09 points, respectively. For P1, P6 and P9, both the MDS-UPDRS motor score and the MDS-UPDRS total score are even lower after 24 weeks than after 8 weeks of treatment.

Figure 17B:
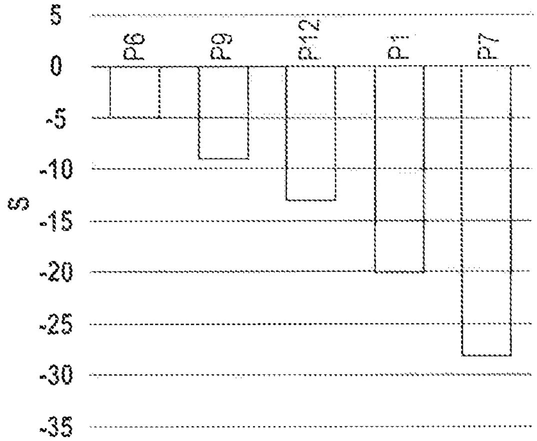

FIG. 17*a* and FIG. 17*b* show the difference between the baseline (BL) and the final assessment (FA) after 24 weeks of the MDS-UPDRS motor score (part III) and the MDS-UPDRS total score, respectively, for each patient (P1, P6, P7, P9 and P12) in descending order. The labels on the Y-axis mean:

R: change in UPDRS motor score ("off" standard medication for 12 h);

S: change in UPDRS total score.

Pharmacokinetics/Pharmacodynamics

The samples of the 9 patients with weekly infusion of 720 mg Talineuren (dose consolidation part) were collected during 10 timepoints during the first infusion (0 min, 5 min, 30 min, 1 h, 4 h, 8 h, 24 h, 48 h, 72 h, 96 h).

| Patient | $t_{max}$ h | $C_{max}$ ng/mL | $t_{1/2}$ h |
|---|---|---|---|
| 4 | 4 | 225000 | 11.3 |
| 5 | 4 | 91900 | 12.6 |
| 6 | 4 | 83900 | 19.1 |
| 7 | 4 | 144000 | 10.9 |
| 8 | 1 | 199000 | 10.2 |
| 9 | 4 | 147000 | 13.2 |
| 10 | 4 | 582000 | 14.8 |
| 11 | 4 | 290000 | 30.7 |
| 12 | 4 | 146000 | 11.9 |
| N | 9 | 9 | 9 |
| Mean | | 212000 | 15.0 |
| SD | | 153000 | 6.46 |
| Min | 1 | 83900 | 10.2 |
| Median | 4 | 147000 | 12.6 |
| Max | 4 | 582000 | 30.7 |
| Coeff. of variance CV % | | 72.2 | 43.2 |
| Geometric mean | | 178000 | 14.1 |
| CV % geom. mean | | 65.2 | 35.8 |

Table 3 shows the time at which the highest blood plasma concentration was reached ($t_{max}$), the highest blood plasma concentration ($c_{max}$) and the half-life ($t_{1/2}$) of GM1 in the blood plasma for each of the nine patients. Further, the mean, the standard deviation (SD), the minimum, the median, the maximum, the coefficient of variance (CV %), the geometric mean and the geometric mean of the coefficient of variance of these values are shown. FIG. 18 shows the GM1 concentration over time in the blood plasma for all nine patients and the mean value of each measured point in time. The labels on the axes mean:

T: time after infusion start in h;

U: GM1 concentration in ng/ml.

GM1 was measured in all samples. Most patients have reached their highest venous blood plasma concentration after 4 h. The infusion lasted 90 min and there was no sampling at that timepoint. Therefore, the highest blood plasma concentration might also be reached earlier. There is still a significantly higher level of GM1 after 96 h compared to the baseline, which confirms the expectation of a long circulating drug.

The mean of the half-life is slightly lower than expected, although there are high individual numbers (patient 11) and a broad standard deviation. There might be no accumulation in the blood plasma with the currently measured mean half-life and a frequency of just one dose per week. It might therefore be interesting to test different dose-frequencies in order to reach a steady-state condition. The mean of the volume of distribution is relatively low and might suggest that GM1 is mostly in the blood. It might also mean, that GM1 is widely distributed to the central nervous system and not to other hydrophobic parts of the body.

Example 4: Brain Penetrance

Talineuren delivery to the brain has been assessed in mice. Fluorescently labelled Talineuren (TLN-DiI) was administered to mice and accumulation of the dye was determined 24 h or 48 h later.

FIG. 19*a* shows TLN-DiI uptake in cells of the substantia nigra of the mouse brain after 48 h (TLN-DiI, i.v., 30 mg/kg). The left image of FIG. 19*a* shows both the nuclear DNA (DAPI, blue) and the DiI dye (red), the right image of FIG. 19*a* shows the DiI dye (red) only. FIG. 19*b* shows TLN-DiI uptake in cells of the motor cortex of the brain after 24 h (TLN-DiI, i.v., 15 mg/kg). The DiI signal was detected in cells of substantia nigra as well as the motor cortex (white arrows).

The accumulation of Talineuren's active pharmaceutical ingredient (GM1) in the rat brain was investigated in a study with CD-1 rats. Each animal received a dose of 12.3 mg/kg body weight of either free (GM1) or liposomal GM1 (TLN) intravenously once per day for 4 consecutive days. GM1 levels were quantified in the brain 24 h after the last dose by liquid chromatography-mass spectrometry/mass spectrometry (LC-MS/MS).

FIG. 20 shows the GM1 levels in the rat brain (V) after four days of treatment. The values were significantly increased in the group that received Talineuren (liposomal GM1; TLN) compared to the group receiving free GM'. This indicates that GM1 is more efficiently delivered to the brain when inserted into the liposome.

The invention claimed is:

1. A method of treating Parkinson's disease in a subject in need thereof, comprising administering to said subject a liposomal composition comprising sphingomyelin in a lipid bilayer and a therapeutically effective amount of GM1, wherein the liposomal surface is completely free of chemically coupled folic acid, peptides, antibodies, sugars, polyethylene glycol, monoclonal antibodies, fractions of monoclonal antibodies, and surface proteins.

2. The method according to claim 1, wherein a therapeutically effective dose of said liposomal composition is administered at most every 4 days in a primary mode of administration with at least 3 days between each administration.

3. The method according to claim 2, wherein the composition is administered intravenously in the primary mode of administration.

4. The method according to claim 3, wherein the dose is administered over a period of between 45 minutes and 90 minutes.

5. The method according to claim 2, wherein the administration in the primary mode of administration is accompanied by administration in a secondary mode of administration in-between doses of the primary mode of administration, wherein the secondary mode of administration is an oral administration.

6. The method according to claim 5, wherein the administration of the primary and/or secondary mode of administration comprises a dosing regimen of equal doses of said liposomal composition comprising GM1.

7. The method according to claim 5, wherein the administration of the primary and/or secondary mode of administration comprises a dosing regimen of increasing doses of said liposomal composition comprising GM1.

8. The method according to claim 2, wherein the primary mode of administration comprises a second dose of said liposomal composition comprising GM1 that is lower than the first dose.

9. The method according to claim 2, wherein the primary mode of administration comprises a second dose of said liposomal composition comprising GM1 that is administered at a lower flow rate than the first dose.

10. The method according to claim 1, wherein said therapeutically effective dose of GM1 of said liposomal composition is between 300 mg and 800 mg.

11. The method according to claim 1, wherein the liposomal composition additionally comprises cholesterol.

12. The method according to claim 2, wherein said therapeutically effective amount of GM1 in said liposomal composition in a single dose of the primary mode of administration is chosen such that it leads to a venous blood plasma concentration of GM1 between 50 μg/ml and 1200 μg/ml.

13. The method according to claim 12, wherein the said venous blood plasma concentration of GM1 is reached within 1 h to 7 h after the start of administration.

14. The method according to claim 1, wherein the liposomes of said liposomal composition have a mean diameter between 10 nm and 70 nm, measured by dynamic light scattering.

15. The method according to claim 1, wherein the liposomes of said liposomal composition have a mean diameter between 10 nm and 50 nm, measured by CryoTEM.

16. The method according to claim 1, wherein the liposomal composition comprises phosphate buffer saline at a pH of about 6.8.

17. The method according to claim 1, wherein the method of treating Parkinson's disease (PD) is selected from reducing tremor, increasing physical movement, increasing walking speed, improving walking ability, improving motion control, and improving speech, in a patient with Parkinson's disease (PD).

* * * * *